(12) United States Patent
Gee et al.

(10) Patent No.: US 10,550,422 B2
(45) Date of Patent: Feb. 4, 2020

(54) METHODS AND COMPOSITIONS FOR LABELING NUCLEIC ACIDS

(71) Applicants: President and Fellows of Harvard College, Cambridge, MA (US); Life Technologies Corporation, Carlsbad, CA (US)

(72) Inventors: Kyle R. Gee, Springfield, OR (US); Brian Agnew, Eugene, OR (US); Adrian Salic, Cambridge, MA (US); Timothy J. Mitchison, Brookline, MA (US)

(73) Assignees: President and Fellows of Harvard College, Cambridge, MA (US); Life Technologies Corporation, Carlsbad, CA (US)

(*) Notice: Subject to any disclaimer, the term of this patent is extended or adjusted under 35 U.S.C. 154(b) by 374 days.

(21) Appl. No.: 15/332,304

(22) Filed: Oct. 24, 2016

(65) Prior Publication Data

US 2017/0137866 A1    May 18, 2017

Related U.S. Application Data

(60) Division of application No. 13/972,365, filed on Aug. 21, 2013, now Pat. No. 9,512,465, which is a
(Continued)

(51) Int. Cl.
C12Q 1/6806 (2018.01)
C12Q 1/68 (2018.01)
(Continued)

(52) U.S. Cl.
CPC ............ *C12Q 1/6806* (2013.01); *C12Q 1/68* (2013.01); *C12Q 1/6816* (2013.01);
(Continued)

(58) Field of Classification Search
None
See application file for complete search history.

(56) References Cited

U.S. PATENT DOCUMENTS 5,430,937 A    7/1995   Leahy et al.
5,810,685 A    9/1998   Willner et al.
(Continued)

FOREIGN PATENT DOCUMENTS

EP         1877415 A2      1/2008
WO      WO-96/09316 A1    3/1996
(Continued)

OTHER PUBLICATIONS

Lee et al. Contacts between 5 S DNA and Xenopus TFIIIA Identified Using 5-Azido-2'-deoxyuridine—substituted DNA. The Journal of Biological Chemistry 266(25):16478-16484. (Year: 1991).*
(Continued)

*Primary Examiner* — Samuel C Woolwine
(74) *Attorney, Agent, or Firm* — Choate, Hall & Stewart LLP; Charles E. Lyon; Xiaodong Li

(57) ABSTRACT

The present invention relates to methods for the labeling of nucleic acid polymers in vitro and in vivo. Certain methods are provided that include a [3+2] cycloaddition between a nucleotide analogue incorporated into a nucleic acid polymer and a reagent attached to a label. Other methods are provided that include a Staudinger ligation between a nucleotide analogue incorporated into a nucleic acid polymer and a reagent comprising a substituted triarylphosphine attached to a label. Such methods do not require fixation and denaturation and therefore can be applied to the labeling of nucleic acid polymers in living cells and in organisms. Also provided are methods for measuring cellular proliferation. In these methods, the amount of label incorporated into the DNA is measured as an indication of cellular proliferation. The methods of the invention can be used in a wide variety
(Continued)

of applications including clinical diagnosis of diseases and disorders in which cellular proliferation is involved, toxicity assays, and as a tool for the study of chromosomes' ultrastructures.

9 Claims, 18 Drawing Sheets

Related U.S. Application Data continuation of application No. 12/785,999, filed on May 24, 2010, now Pat. No. 8,541,570, which is a division of application No. 11/588,697, filed on Oct. 27, 2006, now Pat. No. 7,767,421.

(60) Provisional application No. 60/730,745, filed on Oct. 27, 2005.

(51) Int. Cl.
  *C12Q 1/6816* (2018.01)
  *C12Q 1/6841* (2018.01)
  *G01N 33/50* (2006.01)
  *G01N 33/58* (2006.01)

(52) U.S. Cl.
  CPC ....... *C12Q 1/6841* (2013.01); *G01N 33/5011* (2013.01); *G01N 33/582* (2013.01)

(56) References Cited

U.S. PATENT DOCUMENTS

| | | | |
|---|---|---|---|
| 5,925,517 A | 7/1999 | Tyagi et al. | |
| 5,958,696 A | 9/1999 | Crute | |
| 5,980,263 A | 11/1999 | Conover | |
| 6,083,699 A | 7/2000 | Leushner et al. | |
| 6,464,602 B1 | 10/2002 | Rottger | |
| 6,646,864 B2 | 11/2003 | Richardson | |
| 6,664,047 B1 | 12/2003 | Haugland et al. | |
| 6,737,236 B1 | 5/2004 | Pieken et al. | |
| 7,375,234 B2 | 5/2008 | Sharpless et al. | |
| 7,427,678 B2 | 9/2008 | Pieken et al. | |
| 7,910,335 B2 | 3/2011 | Salic et al. | |
| 8,114,636 B2 | 2/2012 | Agnew et al. | |
| 8,129,315 B2 | 3/2012 | Carell et al. | |
| 8,541,570 B2 | 9/2013 | Gee et al. | |
| 8,859,753 B2 | 10/2014 | Salic et al. | |
| 9,790,541 B2 | 10/2017 | Salic et al. | |
| 2001/0007747 A1* | 7/2001 | Bochkariov | C12Q 1/6816 435/6.18 |
| 2002/0127561 A1 | 9/2002 | Bee et al. | |
| 2004/0023207 A1 | 2/2004 | Polansky | |
| 2004/0197781 A1 | 10/2004 | Sana et al. | |
| 2004/0209317 A1 | 10/2004 | Ting | |
| 2004/0259135 A1 | 12/2004 | Cleary et al. | |
| 2005/0032081 A1 | 2/2005 | Ju et al. | |
| 2005/0148032 A1 | 7/2005 | Saxon et al. | |
| 2006/0147963 A1* | 7/2006 | Barone | C12N 15/1096 435/6.12 |
| 2007/0207476 A1 | 9/2007 | Salic et al. | |
| 2008/0075661 A1 | 3/2008 | Robillard et al. | |
| 2008/0199872 A1 | 8/2008 | Barnard et al. | |
| 2008/0268462 A1 | 10/2008 | Kosmeder et al. | |
| 2012/0107943 A1 | 5/2012 | Carell et al. | |
| 2012/0157327 A1 | 6/2012 | Carell et al. | |
| 2012/0172582 A1 | 7/2012 | Carell et al. | |
| 2012/0190838 A1 | 7/2012 | Carell et al. | |
| 2014/0295414 A1 | 10/2014 | Salic et al. | |
| 2018/0087091 A1 | 3/2018 | Salic et al. | |

FOREIGN PATENT DOCUMENTS

| | | | |
|---|---|---|---|
| WO | WO-1996/009316 A1 | 3/1996 | |
| WO | WO-1996/020289 A1 | 7/1996 | |
| WO | WO-96/34984 A1 | 11/1996 | |
| WO | WO-1996/034984 A1 | 11/1996 | |
| WO | WO-1998/030575 A1 | 7/1998 | |
| WO | WO-2004/055160 A2 | 7/2004 | |
| WO | WO-2006/116629 A2 | 11/2006 | |
| WO | WO-2008/082440 A2 | 7/2008 | |

OTHER PUBLICATIONS

Siebert et al. Application of Interphase Fluorescence in Situ Hybridization for the Detection of the Burkitt Translocation t(8;14)(q24; q32) in B-Cell Lymphomas. Blood 91(3):984-990. (Year: 1998).*
Agard, N. J. et al., A strain-promoted [3+2] azide-alkyne cycloaddition for covalent modification of biomolecules in living systems, J. Am. Chem. Soc., 126:15046-15047 (2004).
Aguilera et al., Permeabilizing action of an antimicrobiallactoferricin-derived peptide on bacterial and artificial membranes, FEBS Lett., 462:273-277 (1999).
Anderson, E. et al., The synthesis of diene-containing nucleoside phosphoramidites and their use in the labeling of oligonucleotides, Nucleosides, Nucleotides and Nucleic Acids, 24:(5/7):761-765 (2005).
Bergstrom et al., Letter: Synthesis of C—5 substituted pyrimidine nucleosides via organopalladium intermediates, J. Am. Chem. Soc., 98:1587-1589 (1976).
Beutler, Cladribine (2-chlorodeoxyadenosine), Lancet, 340:952-956 (1992).
Bleackley et al., The preparation of 5-cyanouracil and 5-cyano-2'-deoxyuridine from the corresponding 5-iodo derivative and cuprous cyanide, Nucleic Acids Res., 2:683-690 (1975).
Bussing et al., Expression of mitochondrial Apo2.7 molecules and caspase-3 activation in human lymphocytes treated with the ribosome-inhibiting mistletoe lectins and the cell membrane permeabilizing viscotoxins, Cytometry, 37:133-139 (1999).
Chen, I., Site-specific labeling of proteins with small molecules in live cells, Current; Opinion in Biotechnology, 16(1):35-40 (2005).
Comstock, L.R. et al., Conversion of DNA methyltransferases into azidonucleosidyl transferases via synthetic cofactors, Nucleic Acids Research, 33(5):1644-1652 (2005).
De Clercq et al., Thymidylate synthetase as target enzyme for the inhibitory activity of 5-substituted 2'-deoxyuridines on mouse leukemia L1210 cell growth, Molecular Pharmacology, 19:321-330 (1981).
De Clerq et al., (E)-5-(2-Bromovinyl)-2'-deoxyuridine: A potent and selective anti-herpes aQent, Proc. Natl. Acad. Sci. USA. 76(6):2947-2951 (1979).
DeClercq, et al., (E)-5-(2-Bromovinyl)-2'-deoxyuridine: A potent and selective anti-herpes agent, Proc. Natl. Acad. Sci. USA. 76(6):2947-2951 (1979).
Deiters et al., In vivo incorporation of an alkyne into proteins in *Escherichia coli*, Bioorganic & Medicinal Chemistry Letters, 15 (5):1521-1524 (2005).
Gallo et al., Oligodendrocyte progenitor cell proliferation and lineage progression are regulated by glutamate receptor-mediated K+ channel block. Journal of Neuroscience 16(8):2659-2670 (1996).
Gierlich, J. et al., Click chemistry as a reliable method for the high-density postsynthetic functionalization of alkyne-modified DNA, Organic Letters, American Chemical Society, US, 8(17):3639-3642 (2006).
Goncalves et al., The use of permeabilized cells to assay protein phosphorylation and catecholamine release, Neurochem. Res., 25:885-894 (2000).
Haralambidis, J. et al., Preparation of base-modified nucleosides suitable for non-radioactive label attachment and their incorporation into synthetic oligodeoxyribonucleotides, Nucleic Acids Research, 15 (12): 4857-4876 (1987).
He et al., Synthesis of 5-substituted 2'-deoxycytidine 5'-(alpha-P-borano)triphosphates, their incorporation into DNA and effects on exonuclease, Nucleic Acids Res., 8:1788-1798 (1999).
Held et al., Challenging artificial genetic systems: thymidine analogs with 5-position sulfur functionality, Nucleic Acids Res., 30:3857-3869 (2002).

(56) References Cited

OTHER PUBLICATIONS

Hellerstein et al., Directly measured kinetics of circulating T lymphocytes in normal and HIV-1-infected humans, Nature Med., 5:83-89 (1999).
Hellerstein, Measurement of T-cell kinetics: recent methodologic advances, Immunol. Today, 20:438-441 (1999).
Higashiya et al., A facile synthesis of 2-azidoadenosine derivatives from guanosine as photoaffinity probes, Bioorganic & Medicinal Chemistry Letters, Oxford, GB., 6 (1): 39-42 (1996).
Hui et al., Gemcitabine: a cytidine analogue active against solid tumors, Am. J. Health Syst. Pharm.,54:162-170 (1997).
International Preliminary Report on Patentability, PCT/US2006/041885 dated Apr. 29, 2008.
International Preliminary Report on Patentability, PCT/US2006/042287 dated Apr. 29, 2008.
International Preliminary Report on Patentability, PCT/US2008/053870, dated Aug. 19, 2009.
International Search Report, PCT/US2006/041885 dated May 4, 2007.
International Search Report, PCT/US2006/042287 dated Nov. 20, 2007.
Iwasaki et al., Differential incorporation of ara-C, gemcitabine, and fludarabine into replicating and repairing DNA in proliferating human leukemia cells., Blood, 90:270-278 (1997).
Jones et al., A method for the rapid preparation of 5-vinyluracil in high yield, Nucleic Acids Res., 1:105-107 (1974).
Kagel et al., A chemical model for the fragmentation reaction in thymidylate synthase catalysis: Synthesis and evaluation of a 5-methylene-1-(1,2,3,4-tetrahydroquinoly1) -6-allyluridine, Journal of Organic Chemistry, 58 (10): 2738-2746 (1993).
Kanda et al., Histone-GFP fusion protein enables sensitive analysis of chromosome dynamics in living mammalian cells, Curr. Biol., 8:377-385 (1998).
Keppler et al., A general method for the covalent labeling of fusion proteins with small molecules in vivo, Nature Biotechnology, 21(1) 86-89 (2003).
Kiick et al., Incorporation of azides into recombinant proteins for chemoselective modification by the Staudinger ligation, Proc. Natl. Acad. Sci. USA, 99:19-24 (2002).
Kohn, M. et al., The Staudinger Litigation—A Gift of Chemical Biology, Angew. Chem. Int. Ed.,; 43:3206-3215 (2004).
Kolb et al., The growing impact of click chemistry on drug discovery, Drug Discovery Today, 8 (24): 1128-1137 (2003).
Kufe et al., Relationships among Ara-CTP pools, formation of (Ara-C)DNA, and cytotoxicity of human leukemic cells, Blood, 64:54-58 (1984).
Langenhan et al., Recent carbohydrate-based chemoselective ligation applications, Current Organic Synthesis, 2 (1):59-81 (2005).
Lemieux et al., A fluorogenic dye activated by the staudinger ligation, J. Am. Chem. Soc.,125:4708-4709 (2003).
Lewis et al., Click chemistry in situ: acetylcholinesterase as a reaction vessel for the selective assembly of a femtomolar inhibitor from an array of building blocks, Angew Chem. Int. Ed. Engl., 41:1053-1057 (2002).
Macallan et al., Measurement of cell proliferation by labeling of DNA with stable isotope-labeled glucose: studies in vitro, in animals, and in humans, Proc. Natl. Acad. Sci. USA, 95:708-713 (1998).
Makabe et al., Synthesis of some nucleoside analogs of substituted 1,2,3-triazole. Bulletin of the Chemical Society of Japan, 45:2577-9 (1972).
Mao et al., Profound astrogenesis in the striatum of adult mice following nigrostriatal dopaminergic lesion by repeated MPTP administration. Developmental Brain Research 131:57-65 (2001).
Maranto, Neuronal mapping: a photooxidation reaction makes Lucifer yellow useful for electron microscopy, Science, 217:953-955 (1982).
Marsh et al., The synthesis and properties of oligoribonucleotide-spermine conjugates, Organic and Biomolecular Chemistry, 2 (14):2013-2112 (2004).
Minakawa et al., A versatile modification of on-column oligodeoxynucleotides using a copper-catalyzed oxidative acetylenic coupling reaction, Journal of the American Chemical Society, 125(38):11545-11552 (2003).
Mutasa, Osmium tetroxide-potassium ferrocyanide intensification of a diaminobenzidine product obtained by photoconversion of a fluorescent label: a study of human neutrophil granules, Biotech. Histochem., 70: 94-201 (1995).
Nguyen et al., Studies towards the design of a modified gc base pair with stability similar to that of the at base pair, Tetrahedron Letters, 38 (23):4083-4086 (1997).
Otvos et al., Base Modified Oligodeoxynucleotides. II. Increase of Stability to Nucleases by 5- Alkyl-, 5-(1-Aikenyl)-, and 5-(1-Aikynyl)-pyrimidines, Nucleosides, Nucleotides and Nucleic Acids, 18(9):1929-1933 (1999).
Package Insert for Chemicon International's TraPexe Telomerase Detection Kit, 1-39 (2003-2005).
Prescher et al., Chemical remodelling of cell surfaces in living animals, Nature, 430:873-877 (2004).
Restituyo, J.A. et al., Conversion of Aryl Azides to O-Alkyl Imidates via Modified Staudinger Ligation, Organic Letters, 5(23): 4357-4360 (2003).
Ribeiro et al., Modeling deuterated glucose labeling of T-lymphocytes, Bull. Math. Bioi., 64:385-405 (2002).
Rodionov et al., Mechanism of the Ligand-Free CuI-Catalyzed Azide-Alkyne Cycloaddition Reaction, Angewandte Chemie International Edition, 44 (15): 2210-2215 (2005).
Rostovtsev et al., A stepwise huisgen cycloaddition process: copper(I)-catalyzed regioselective "ligation" of azides and terminal alkynes, Angew Chem., Int. Ed. Engl., 41:2596-2599 (2002).
Saxon et al., A "traceless" Staudinger ligation for the chemoselective synthesis of amide bonds, Org. Lett., 2:2141-214 (2000).
Saxon et al., Cell surface engineering by a modified Staudinger reaction, Science, 287:2007-2010 (2000).
Seo et al., Click chemistry to construct fluorescent oligonucleotides for DNA sequencing, J. Org. Chem. 68:609-612 (2003).
Shealy et al., Carbocyclic analogues of 5-substituted uracil nucleosides: synthesis and antiviral activity, J. Med. Chem., 26:156-161 (1983).
Soellner et al., Reaction mechanism and kinetics of the traceless staudinger ligation, J. Am. Chem. Soc., 128:8820-8828 (2006).
Speers et al., Profiling enzyme activities in vivo using click chemistry methods, Chemistry & Biology, 11:535-546 ( 2004).
Summerer et al., 4'C-ethynyl-thymidine acts as a chain terminator during DNA-synthesis catalyzed by HIV-1 reverse transcriptase, Bioorganic & Medicinal Chemistry Letters, 15:869-871 (2005).
Sunthankar et al., Synthesis of 5-azido-UDP-N-acetylhexosamine photoaffinity analogs and radiolabeled UDP-N-cetylhexosamines, Anal. Biochem., 258:195-201 (1998).
Supplementary European Search Report for EP06836555.0, dated Feb. 7, 2013.
Supplementary European Search Report for EP06836555.0, 5 pages dated Jul. 2, 2013.
Supplementary European Search Report for EP06851143.5, dated Feb. 7, 2013.
Sylvers et al., Nucleic acid-incorporated azidonucleotides: probes for studying the interaction of RNA or DNA with proteins and other nucleic acids, Bioconjugate Chemistry, 4(6):411-418 (1993).
Trevisiol et al., The oxyamino-aldehyde coupling reaction: an efficient method for the derivatization of oligonucleotides, Tetrahedron Letters, 38 (50): 8687-8690 (1997).
Van De Bor et al., mRNA localisation gets more complex, Curr. Opin. Cell Biol., 16:300-307 (2004).
Venyaminova et al., New photoreactive mRNA analogues for the affinity labeling of ribosomes Nucleosides and Nucleotides, 14 ( 3-5): 1069-1072 (1995).
Wang et al., Bioconjugation by copper(I)-catalyzed azide-alkyne [3+2] cycloaddition, J. Am. Chem. Soc.,125:3192-3193 (2003).
Wang, C.C.-Y. et al., Site-Specific Fluorescent Labeling of DNA Using Staudinger Litigation, Bioconjugate Chem., 14:697-701 (2003).

* cited by examiner

METHODS AND COMPOSITIONS FOR LABELING NUCLEIC ACIDS

RELATED APPLICATIONS

This application is a divisional of U.S. patent application Ser. No. 13/972,365, filed Aug. 21, 2013 know U.S. Pat. No. 9,512,465), which is a continuation of U.S. patent application Ser. No. 12/785,999, filed May 24, 2010 (now U.S. Pat. No. 8,541,570), which is a divisional of U.S. patent application Ser. No. 11/588,697, filed Oct. 27, 2006 (now U.S. Pat. No. 7,767,421), which claims priority to U.S. Patent Application No. 60/730,745, filed Oct. 27, 2005, the entirety of each of which is hereby incorporated by reference.

GOVERNMENT SUPPORT

Part of the work described herein was funded by the National Institutes of Health (Grant No. GM039565).

BACKGROUND OF THE INVENTION

Cell division and cell death play central roles in the proper development of multicellular organisms and in the homeostatic maintenance of tissues. Loss or reduction of cell proliferative capability and dysregulation of cell death are among the most important phenomena that characterize the aging process (D. Monti et al., Am. J. Clin. Nutr., 1992, 55 (6 Suppl): 1208S-1214S; H. R. Warner et al., J. Am. Geriatr. Soc., 1997, 45: 1140-1146; L. Ginaldi et al., Immunol. Res., 2000, 21: 31-38). Disruption of normal control of cell proliferation and cell death also underlies many pathological conditions including cancer; infectious diseases such as acquired immunodeficiency syndrome (J. C. Bentin et al., J. Clin. Immunol., 1989, 9: 159-168; R. A. Gruters et al., Eur. J. Immunol., 1990, 20: 1039-1044; L. Mcyaard et al., Science, 1992, 257: 217-119; A. Cayota et al., Clin. Exp. Immunol., 1992, 88: 478-483); vascular disorders such as atherosclerosis and hypertension (S. M. Schwartz et al., Circ. Res., 1986, 58: 427-444; A. Rivard and V. Andres, Histol. Histopathol., 2000, 15: 557-571); and neurodegenerative diseases such as Alzheimer's disease (Z. Nagy, J. Neural Transm. Suppl., 1999, 57: 233-245; A. K. Raina et al., Prog. Cell Cycle Res., 2000, 4: 235-242; I. Vincent et al., Prog. Cell Cycle Res., 2003, 5: 31-41).

The most characteristic biochemical feature of cell division is DNA synthesis, which occurs essentially only during the S phase of the cell cycle (S. Sawada et al., Mutat. Res., 1995, 344: 109-116). Accordingly, the most commonly used methods for the study of cell cycle, DNA synthesis and cell proliferation rely on incorporation of labeled biosynthetic precursors into the newly synthesized DNA of proliferating cells (M. Bick and R. L. Davidson, Proc. Natl. Acad. Sci. USA, 1974, 71: 2082-2086; H. G. Gratzner, Science, 1982, 218: 474-475; F. M. Waldman et al., Mod. Pathol., 1991, 4: 718-722). In these methods, labeled DNA precursors (e.g., [$^3$H]-thymidine or 5-bromo-2'-deoxyuridine (BrdU)) are added to cells during replication, and their incorporation into genomic DNA is quantified following incubation and sample preparation. Incorporated [H]-thymidine is generally detected by autoradiography. Detection of incorporated BrdU is performed immunologically after sample denaturation to allow access of monoclonal antibodies, and the resulting BrdU-labeled cells are then analyzed by flow cytometry or microscopy. To study cellular proliferation of specific tissues, animals are administered (e.g., injected) labeled DNA precursors, sacrificed, and the tissues are removed and fixed for microscopic analysis.

Although [$^3$H]-thymidine and BrdU incorporation labeling methods have proven valuable for studying cell cycle kinetics, DNA synthesis and sister chromatid exchange, as well as for assessing cell proliferation of normal or pathological cells or tissues under different conditions, these methods exhibit several limitations. The most notable disadvantage of [$^3$H]-thymidine incorporation results from the complications and risks of using radioactivity. In addition, autoradiography is labor-intensive and time-consuming. Furthermore, because both methods are sample destructive, quantification can be performed at only one predetermined time point, and continuous monitoring of a single sample is not possible. Additionally, in contrast to [$^3$H]-thymidine autoradiography, BrdU immunohistochemistry is not stoichiometric (R. S. Nowakowski et al., J. Neurocytol., 1989, 18: 311-318; R. S. Nowakowski and N. L. Hayes, Science, 2000, 288: 771). Thus, the intensity or extent of labeling is highly dependent on the conditions used for detection and does not necessarily reflect the magnitude of DNA replication. For this reason, BrdU labeling as a measure of cell division is especially vulnerable to misinterpretation (P. Rakic, Nature Rev. Neurosci., 2002, 3: 56-71).

More recently, a stable isotope-mass spectrometric technique has been developed that resolves some of the problems associated with the [$^3$H]-thymidine and BrdU incorporation methods (D. C. Macallan et al., Proc. Natl. Acad. Sci. USA, 1998, 95: 708-713; M. K. Hellerstein, Immunol. Today, 1999, 20: 438-441; M. Hellerstein et al., Nature Med., 1999, 5: 83-89; J. M. McCune et al., J. Clin. Invest., 2000, 105: RI-8; H. Mohri et al., J. Exp. Med., 2001, 94: 1277-1288; R. M. Ribeiro et al., Proc. Natl. Acad. Sci. USA, 2002, 99: 15572-15577, R. M. Ribeiro et al., Bull. Math. Biol., 2002, 64: 385-405). In this technique, the deoxyribose moiety of nucleotides in replicating DNA is labeled endogenously, through the de novo nucleotide synthesis pathway by using stable isotope $^2$H- or $^{13}$C-labeled glucose. The isotopic enrichment of the DNA is then detected and quantified by gas chromatographic/mass spectrometric (GC/MS) analysis after isolation, denaturation and hydrolysis of genomic DNA and TMS (trimethylsyl) derivatization of the resulting deoxyribonucleosides. Although this method has several advantages including being safe for use in humans, it has disadvantages including that it involves a lengthy and destructive processing of the sample prior to detection.

Clearly, improved nucleic acid labeling techniques are still needed for the study of cell cycle kinetics, DNA synthesis and cellular proliferation in vitro and in vivo. In particular, the development of techniques that are simple, rapid, and sensitive and that do not require extensive sample preparation and/or do not result in sample destruction remains highly desirable.

SUMMARY OF THE INVENTION

The present invention is directed to improved systems and strategies for studying cell division. More specifically, the present invention provides methods and compositions useful for labeling nucleic acid molecules and for measuring cellular proliferation in vitro and in vivo. In general, the inventive methods include a chemical reaction between a nucleotide analogue incorporated into a nucleic acid polymer and a reagent comprising a label, wherein the nucleotide analogue contains a first reactive group and the reagent contains a second reactive group such the reaction between the first and second reactive groups results in the labeling of the nucleic acid polymer. Such methods do not require extensive processing of the labeled sample. In particular, many inventive methods do not require denaturation of the sample. In particular, the present invention provides methods of labeling nucleic acid polymers that include a [3+2] cycloaddition between a nucleotide analogue incorporated into a nucleic acid polymer and a reagent comprising a label and methods of labeling nucleic acid polymers that include a Staudinger ligation reaction between a nucleotide analogue incorporated into a nucleic acid polymer and a reagent comprising a label.

More specifically, in one aspect, the present invention provides methods for labeling a nucleic acid polymer, comprising steps of: providing a nucleic acid polymer containing at least one nucleotide analogue that comprises a first reactive unsaturated group; and contacting the nucleic acid polymer with a reagent comprising a second reactive unsaturated group attached to a label, such that a [3+2] cycloaddition occurs between the first and second unsaturated groups.

In certain embodiments, the first reactive unsaturated group comprises a 1,3-dipole and the second reactive unsaturated group comprises a dipolarophile. In other embodiments, the first reactive unsaturated group comprises a dipolarophile and the second reactive unsaturated group comprises a 1,3-dipole. In some embodiments, the 1,3-dipole may comprise an azide group and the dipolarophile may comprise an ethynyl group.

In certain embodiments, the label is directly detectable. For example, the label comprises a fluorescent agent. In other embodiments, the label is indirectly detectable. For example, the label comprises a hapten.

The nucleic acid polymer to be labeled may be inside a cell, in a tissue or an organism.

In certain embodiments, the at least one nucleotide analogue is incorporated into the nucleic acid polymer during DNA replication or DNA transcription.

In certain embodiments, the step of contacting the nucleic acid polymer with a reagent is performed under aqueous conditions. The contacting may be performed in the presence of Cu(I). Alternatively, the contacting may be performed in the absence of Cu(I) with a reagent that further comprises a Cu chelating moiety.

In another aspect, the present invention provides methods for dually labeling a nucleic acid polymer. The inventive methods comprise steps of: providing a nucleic acid polymer containing at least one first nucleotide analogue that comprises a first reactive unsaturated group and at least one second nucleotide analogue that comprises a second reactive unsaturated group; contacting the nucleic acid polymer with a first reagent comprising a third reactive unsaturated group attached to a first label, such that a [3+2] cycloaddition occurs between the first and third unsaturated groups; and contacting the nucleic acid polymer with a second reagent comprising a fourth reactive unsaturated group attached to a second label, such that a [3+2] cycloaddition occurs between the second and fourth unsaturated groups.

In certain embodiments, the first reactive unsaturated group comprises a first 1,3-dipole and the third reactive unsaturated group comprises a first dipolarophile; the second reactive unsaturated group comprises a second dipolarophile and the fourth reactive unsaturated group comprises a second 1,3-dipole.

In other embodiments, the first reactive unsaturated group comprises a first dipolarophile and the third reactive unsaturated group comprises a first 1,3-dipole; the second reactive unsaturated group comprises a second 1,3-dipole and the fourth reactive unsaturated group comprises a second dipolarophile. As described above, a 1,3-dipole may comprise an azide group, and a dipolaraphile may comprise an ethynyl group.

In certain embodiments, the first and second labels are directly detectable. In some such embodiments, the first label comprises a first fluorescent agent, the second label comprises a second fluorescent agent, and the first and second fluorescent agents produce a dual-color fluorescence upon excitation.

In other embodiments, the first and second labels are indirectly detectable. For example, the first label comprises a first hapten and the second label comprises a second hapten.

As mentioned above, the nucleic acid polymer to be dually labeled may be inside a cell, in a tissue or an organism; and the first and second nucleotide analogues may be incorporated into the nucleic acid polymer during DNA replication or DNA transcription.

In these inventive methods, the steps of contacting may be performed simultaneously or sequentially. Preferably, the steps of contacting are performed under aqueous conditions.

In another aspect, the present invention provides methods for differentially labeling nucleic acid polymers. These inventive methods comprise steps of: providing a first nucleic acid polymer containing at least one first nucleotide analogue that comprises a first reactive unsaturated group; providing a second nucleic acid polymer containing at least one second nucleotide analogue that comprises a second reactive unsaturated group; contacting the first nucleic acid polymer with a first reagent comprising a third reactive unsaturated group attached to a first label, such that a [3+2] cycloaddition occurs between the first and third unsaturated groups; and contacting the second nucleic acid polymer with a second reagent comprising a fourth reactive unsaturated group attached to a second label, such that a [3+2] cycloaddition occurs between the second and fourth unsaturated groups.

The first and second reactive unsaturated groups and first and second labels may be as described above. As described above, the steps of contacting may be performed simultaneously or sequentially.

In certain embodiments, the first nucleic acid polymer is inside a first cell and the second polymer is inside a second cell. In other embodiments, the first nucleic acid polymer is in a first tissue and the second nucleic acid polymer is in a second tissue. In still other embodiments, the first nucleic acid polymer is in a first organism and the second polymer is in a second organism.

In another aspect, the present invention provides nucleic acid polymers comprising at least one nucleotide analogue attached to a label. Preferably, the nucleic acid polymers are prepared by one of the labeling methods disclosed herein.

In certain embodiments, the nucleotide analogue incorporated into an inventive nucleic acid polymer comprises a cycloadduct, such as a cycloadduct resulting from a [3+2] cycloaddition between an ethynyl group and an azide group.

In certain embodiments, the label is covalently attached to the nucleotide analogue.

In certain embodiments, the label is directly detectable. For example, the label is a fluorescent agent. In other embodiments, the label is indirectly detectable. For example, the label comprises a hapten.

The present invention also provides dually labeled nucleic acid polymers. More specifically, the present invention provides nucleic acid polymers comprising at least one first nucleotide analogue attached to a first label and at least one second nucleotide analogue attached to a second label. Preferably, such nucleic acid polymers are prepared by the dual labeling methods described herein.

In certain embodiments, the at least one first nucleotide analogue comprises a first cycloadduct resulting from a [3+2] cycloaddition between a first ethynyl group and a first azide group and the at least one second nucleotide analogue comprises a second cycloadduct resulting from a [3+2] cycloaddition between a second ethynyl group and a second azide group.

In certain embodiments, the first label comprises a first fluorescent agent, the second label comprises a second fluorescent agent, and the first and second fluorescent agent produce a dual fluorescence upon excitation.

In another aspect, the present invention provides cells comprising one or more inventive labeled or dually labeled nucleic acid polymers.

In still another aspect, the present invention provides kits for labeling a nucleic acid polymer comprising: at least one nucleoside analogue that comprises a first reactive unsaturated group; and a reagent comprising a second reactive unsaturated group attached to a label.

In certain embodiments, the first reactive unsaturated group comprises a 1,3-dipole, the second reactive unsaturated group comprises a dipolarophile and the first and second reactive unsaturated groups can react via [3+2] cycloaddition. In other embodiments, the first reactive unsaturated group comprises a dipolarophile, the second reactive unsaturated group comprises a 1,3-dipole, and the first and second reactive unsaturated groups can react via [3+2]cycloaddition.

The present invention also provides kits for dually labeling a nucleic acid polymer, comprising: at least one first nucleoside analogue that comprises a first reactive unsaturated group; at least one second nucleoside analogue that comprises a second reactive unsaturated group; a first reagent comprising a third reactive unsaturated group attached to a first label; and a second reagent comprising a fourth reactive unsaturated group attached to a second label.

In certain embodiments, the first reactive unsaturated group comprises a first 1,3-dipole, the third reactive unsaturated group comprises a first dipolarophile, and the first and third reactive unsaturated groups can react via [3+2] cycloaddition; the second reactive unsaturated group comprises a dipolarophile, the fourth reactive unsaturated group comprises a second 1,3-dipole, and the second and fourth reactive unsaturated groups can react via [3+2]cycloaddition.

In other embodiments, the first reactive unsaturated group comprises a first dipolarophile, the third reactive unsaturated group comprises a first 1,3-dipole, and the first and third reactive unsaturated groups can react via [3+2] cycloaddition; the second reactive unsaturated group comprises a dipolarophile, the fourth reactive unsaturated group comprises a second 1,3-dipole, and the second and fourth reactive unsaturated groups can react via [3+2]cycloaddition. The inventive kits may further comprise aqueous medium and/or Cu(I).

In still another aspect, the present invention provides methods for measuring cellular proliferation in a cell or in an organism.

Certain inventive methods comprise steps of: contacting a cell with an effective amount of a nucleoside analogue that comprises a first reactive unsaturated group such that the nucleoside analogue is incorporated into DNA of the cell; contacting the cell with a reagent comprising a second reactive unsaturated group attached to a label, such that a [3+2]cycloaddition occurs between the first and second reactive unsaturated groups; and determining an amount of label incorporated into the DNA to measure cellular proliferation. The cell may be in a multi-well assay plate.

Other inventive methods comprise steps of: administering to an organism an effective amount of a nucleoside analogue that comprises a first reactive unsaturated group such that the nucleoside analogue is incorporated into DNA of cells of the organism; contacting at least one cell of the organism with a reagent comprising a second reactive unsaturated group attached to a label, such that a [3+2] cycloaddition occurs between the first and second reactive unsaturated groups; and determining an amount of label incorporated into the DNA to measure cellular proliferation in the organism.

The first and second reactive unsaturated groups; labels and contacting steps in these methods may be as described above.

In yet another aspect, the present invention provides methods for identifying an agent that perturbs cellular proliferation in a cell or in an organism.

Certain inventive methods comprise steps of: (a) contacting a cell with a test agent; (b) contacting the cell with an effective amount of a nucleoside analogue that comprises a first reactive unsaturated group such that the nucleoside analogue is incorporated into DNA of the cell; (c) contacting the cell with a reagent comprising a second reactive unsaturated group attached to a label, such that a [3+2] cycloaddition occurs between the first and second reactive unsaturated groups; (d) determining an amount of label incorporated into the DNA, wherein the amount of label indicates the extent of cellular proliferation; and (e) identifying the test agent as an agent that perturbs cellular proliferation if the amount of label measured in step (d) is less than or greater than the amount of label measured in a control application in which the cell is not contacted with the test agent. Step (b) may be performed before step (a).

Other inventive methods comprise steps of: (a) exposing an organism to a test agent; (b) administering to the organism an effective amount of a nucleoside analogue that comprises a first reactive unsaturated group such that the nucleoside analogue is incorporated into DNA of cells of the organism; (c) contacting at least one cell of the organism with a reagent comprising a second reactive unsaturated group attached to a label, such that a [3+2] cycloaddition occurs between the first and second reactive unsaturated groups; (d) determining an amount of label incorporated into the DNA, wherein the amount of label indicates the extent of cellular proliferation; and (e) identifying the test agent as an agent that perturbs cellular proliferation in the organism if the amount of label measured in step (d) is less than or greater than the amount of label measured in a control application in which the organism is not exposed to the test agent. Step (b) may be performed before step (a). The step of contacting may be performed in vivo or er vivo.

The inventive methods for identifying an agent that perturb cellular proliferation may further comprise: a step of identifying the test agent as an agent that induces cellular proliferation if the amount of label measured in step (d) is greater than the amount of label measured in the control application; and/or a step of identifying the test agent as an agent that inhibits cellular proliferation if the amount of label measured in step (d) is less than the amount of label measured in the control application.

Furthermore, in another aspect, the present invention provides methods for labeling a nucleic acid polymer, comprising steps of: providing a nucleic acid polymer comprising at least one nucleotide analogue that comprises an azide group; and contacting the nucleic acid polymer with a reagent comprising a label attached to a substituted triarylphosphine, such that a Staudinger ligation occurs between the azide and triarylphosphine.

In certain embodiments, one of the aryl groups of the triarylphosphine is substituted with a functional group that acts as an electrophilic trap, such as an alkyl ester (e.g., a methyl ester). Preferably, one of the aryl groups of the triarylphosphine is derivatized with an alkyl ester ortho to the phosphorus atom.

In certain embodiments, the label is directly detectable. For example, the label comprises a fluorescent agent. In other embodiments, the label is indirectly detectable. For example, the label comprises a hapten.

The nucleic acid polymer to be labeled may be an isolated nucleic acid polymer or may be inside a cell, in a tissue or an organism.

In certain embodiments (e.g., when the nucleic acid polymer is inside a cell or in an organism), the at least one nucleotide analogue is incorporated into the nucleic acid polymer during DNA replication or DNA transcription.

In another aspect, the present invention provides methods for differentially labeling nucleic acid polymers. These inventive methods comprise steps of: providing a first nucleic acid polymer comprising at least one first nucleotide analogue that comprises a first azide group; providing a second nucleic acid polymer comprising at least one second nucleotide analogue that comprises a second azide group; contacting the first nucleic acid polymer with a first reagent comprising a first label attached to a first substituted triarylphosphine, such that a Staudinger ligation occurs between the first azide and first triarylphosphine; and contacting the second nucleic acid polymer with a second reagent comprising a second label attached to a second substituted triarylphosphine, such that a Staudinger ligation occurs between the second azide and second triarylphosphine.

In certain embodiments, one of the aryl groups of the first triarylphosphine and one of the aryl groups of the second triarylphosphine are each substituted with a functional group that acts as an electrophilic trap, such as an alkyl ester (e.g., a methyl ester). Preferably, one of the aryl groups of the first triarylphosphine and one of the aryl groups of the second triarylphosphine are each derivatized with an alkyl ester ortho to the phosphorus atom.

In certain embodiments, the first and second labels are directly detectable. In some such embodiments, the first label comprises a first fluorescent agent, the second label comprises a second fluorescent agent, and the first and second fluorescent agents produce a dual-color fluorescence upon excitation.

In other embodiments, the first and second labels are indirectly detectable. For example, the first label comprises a first hapten and the second label comprises a second hapten.

In these methods, the steps of contacting are preferably performed sequentially.

In certain embodiments, the first nucleic acid polymer is inside a first cell and the second nucleic acid polymer is inside a second cell. In other embodiments, the first nucleic acid polymer is in a first tissue and the second nucleic acid polymer is in a second tissue. In still other embodiments, the first nucleic acid polymer is in a first organism and the second polymer is in a second organism.

In another aspect, the present invention provides nucleic acid polymers comprising at least one nucleotide analogue attached to a label. Preferably, the inventive nucleic acid polymers are prepared by one of the labeling methods disclosed herein comprising a Staudinger ligation.

In certain embodiments, the nucleic acid polymer comprises a nucleotide analogue attached to a label through an amide and a triarylphosphine oxide, wherein the amide and triarylphosphine oxide result from a Staudinger ligation reaction.

In certain embodiments, the label is directly detectable. For example, the label is a fluorescent agent. In other embodiments, the label is indirectly detectable. For example, the label comprises a hapten.

In still another aspect, the present invention provides kits for labeling a nucleic acid polymer comprising: at least one nucleoside analogue that comprises an azide group; and a reagent comprising a label attached to a substituted triarylphosphine.

In certain embodiments, one of the aryl groups of the triarylphosphine is substituted with a functional group that acts as an electrophilic trap, such as an alkyl ester. Preferably, one of the aryl groups is derivatized with an alkyl ester ortho to the phosphorus atom. The label may be directly detectable (e.g., the label comprises a fluorescent agent) or indirectly detectable (e.g., the label comprises a hapten).

In still another aspect, the present invention provides methods for measuring cellular proliferation in a cell or in an organism.

Certain inventive methods comprise steps of: contacting a cell with an effective amount of a nucleoside analogue that comprises an azide group such that the nucleoside analogue is incorporated into DNA of the cell; contacting the cell with a reagent comprising a label attached to a substituted triarylphosphine, such that a Staudinger ligation occurs between the azide and triarylphosphine; and determining an amount of label incorporated into the DNA to measure cellular proliferation. The cell may be in a multi-well assay plate.

Other inventive methods comprise steps of: administering to an organism an effective amount of a nucleoside analogue that comprises an azide group such that the nucleoside analogue is incorporated into DNA of cells of the organism; contacting at least one cell of the organism with a reagent comprising a label attached to a substituted triarylphosphine, such that a Staudinger ligation occurs between the azide and triarylphosphine; and determining an amount of label incorporated into the DNA to measure cellular proliferation in the organism. The step of contacting may be performed in vivo or ex vivo.

In certain embodiments of these methods, one of the aryl groups of the triarylphosphine is substituted with a functional group that acts as an electrophilic trap, such as an alkyl ester. Preferably, one of the aryl groups is derivatized with an alkyl ester ortho to the phosphorus atom. The label may be directly detectable (e.g., the label comprises a fluorescent agent) or indirectly detectable (e.g., the label comprises a hapten).

In yet another aspect, the present invention provides methods for identifying an agent that perturbs cellular proliferation in a cell or in an organism.

Certain inventive methods comprise steps of: (a) contacting a cell with a test agent; (b) contacting the cell with an effective amount of a nucleoside analogue that comprises an azide such that the nucleoside analogue is incorporated into DNA of the cell; (c) contacting the cell with a reagent comprising a label attached to a substituted triarylphosphine, such that a Staudinger ligation occurs between the azide and triarylphosphine; (d) determining an amount of label incorporated into the DNA, wherein the amount of label indicates the extent of cellular proliferation; and (e) identifying the test agent as an agent that perturbs cellular proliferation if the amount of label measured in step (d) is less than or greater than the amount of label measured in a control application in which the cell is not contacted with the test agent. In certain embodiment step (b) is performed prior to step (a).

Other inventive methods comprise steps of: (a) exposing an organism to a test agent; (b) administering to the organism an effective amount of a nucleoside analogue that comprises an azide such that the nucleoside analogue is incorporated into DNA of cells of the organism; (c) contacting at least one cell of the organism with a reagent comprising a label attached to a substituted triarylphosphine, such that a Staudinger ligation occurs between the azide and triarylphosphine; (d) determining an amount of label incorporated into the DNA, wherein the amount of label indicates the extent of cellular proliferation; and (e) identifying the test agent as an agent that perturbs cellular proliferation in the organism if the amount of label measured in step (d) is less than or greater than the amount of label measured in a control application in which the organism is not exposed to the test agent. In certain embodiments of the methods, step (b) is performed before step (a). The step of contacting may be performed in vivo or ex vivo.

The inventive methods for identifying a test agent that perturbs cellular proliferation may further comprise the step of identifying the test agent as an agent that induces cellular proliferation if the amount of label measured in step (d) is greater than the amount of label measured in the control application; and/or the step of identifying the test agent as an agent that inhibits cellular proliferation if the amount of label measured in step (d) is less than the amount of label measured in the control application.

These and other objects, advantages and features of the present invention will be apparent to those of ordinary skill in the art in reading the following detailed description.

DEFINITIONS

Figure 1A:
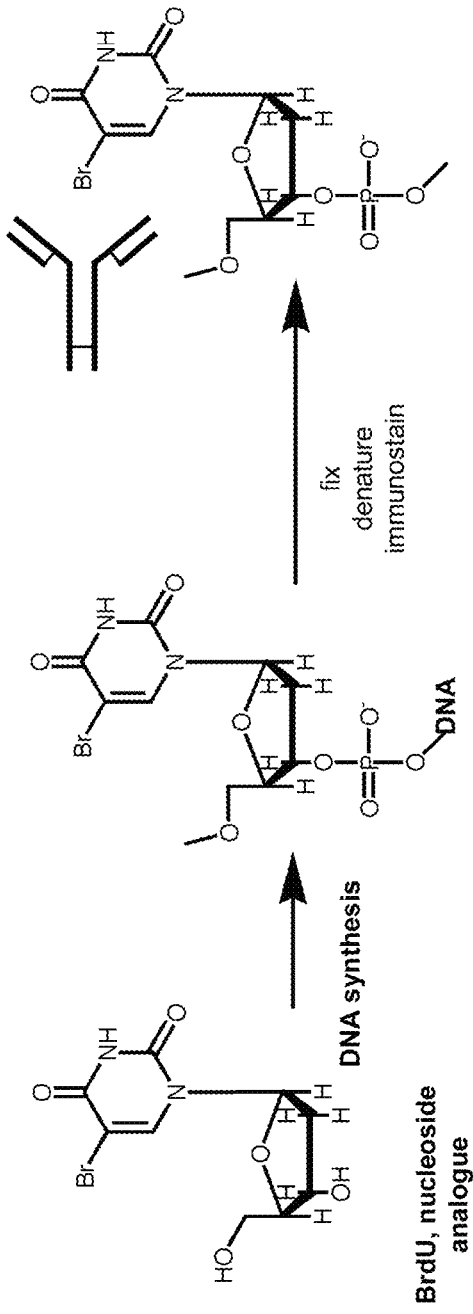
FIG. 1 presents two schemes showing (A) DNA labeling using BrdU as known in the art, and (B) DNA labeling using a method of the present invention that includes incorporation of the nucleoside analogue EdU (i.e., ethynyl-dU) into DNA by DNA replication followed by [3+2] cycloaddition between the ethynyl group and the azide reagent in the presence of Cu(I).

For purpose of convenience, definitions of a variety of terms used throughout the specification are presented below.

The term "nucleic acid polymer" refers to a deoxyribonucleotide or ribonucleotide polymer in either single- or double-stranded form, including DNA and RNA, and unless otherwise stated encompasses nucleic acid-like structures with synthetic backbones, as well as amplification products. In the context of the present invention, a nucleic acid polymer may be an isolated molecule, or, alternatively, a nucleic acid polymer may be located inside a cell or in an organism.

The term "isolated", when used herein in reference to a nucleic acid polymer, means a nucleic acid polymer, which by virtue of its origin or manipulation is separated from at least some of the components with which it is naturally associated or with which it is associated when initially obtained. By "isolated", it is alternatively or additionally meant that the nucleic acid polymer of interest is produced or synthesized by the hand of man.

As used herein, the term "nucleotide analogue" refers to a molecule that is structurally similar to a natural nucleotide and that can function in a similar manner as the naturally occurring nucleotide (e.g., exhibits similar ability to base pair with one of the naturally occurring bases). The term "nucleoside analogue", as used herein, refers to a molecule that is structurally similar to a natural nucleoside and that can function in a similar manner as the naturally occurring nucleoside (e.g., exhibits similar ability to be incorporated into DNA by DNA replication). The term "nucleotide" refers to a monomeric unit of DNA or RNA containing a sugar moiety (pentose), a phosphate and a nitrogenous heterocyclic base. The base is linked to the sugar moiety via the glycosidic carbon (i.e., the 1'-carbon of the pentose) and that combination of base and sugar is called a "nucleoside". The base characterizes the nucleotide (or nucleoside) with the four bases of DNA being adenine (or A), guanine (G), cytosine (C) and thymine (T), and the four bases of RNA being adenine, guanine, cytosine, and uracil (U). In certain embodiments of the present invention a nucleotide analogue (or nucleoside analogue) comprises a reactive unsaturated group.

As used herein, the term "reactive unsaturated group" refers to a functional group containing atoms sharing more than one valence bond and that can undergo addition reactions, in particular cycloadditions. A reactive unsaturated group typically possesses at least one double or triple bond.

The term "1,3-dipole" has herein its art understood meaning and refers to a molecule or functional group that is isoelectronic with the allyl anion and has four electrons in a $\pi$ system encompassing the 1,3-dipole. 1,3-Dipoles generally have one or more resonance structures showing the characteristic 1,3-dipole. Examples of 1,3-dipoles include nitrile oxides, azides, diazomnethanes, nitrones, and nitrile imines.

As used herein, the term "dipolarophile" has its art understood meaning and refers to a molecule or functional group that contains a $\pi$ bond and that exhibits reactivity toward 1,3-dipoles. The reactivity of dipolarophiles depends both on the substituents present on the $\pi$ bond and on the nature of the 1,3-dipole involved in the reaction. Dipolarophiles are typically alkenes or alkynes.

As used herein, the term "cycloaddition" refers to a chemical reaction in which two or more $\pi$-electron systems (e.g., unsaturated molecules or unsaturated parts of the same molecule) combine to form a cyclic product in which there is a net reduction of the bond multiplicity. In a cycloaddition, the $\pi$ electrons are used to form new $\sigma$ bonds. The product of a cycloaddition is called an "adduct" or "cycloadduct". Different types of cycloadditions are known in the art including, but not limited to, [3+2] cycloadditions and Diels-Alder reactions. [3+2] cycloadditions, which are also called 1,3-dipolar cycloadditions, occur between a 1,3-dipole and a dipolarophile and are typically used for the construction of five-membered heterocyclic rings. The term "[3+2] cycloaddition" also encompasses "copperless" [3+2] cycloadditions between azides and cyclooctynes and difluorocyclooctynes described by Bertozzi et al., J. Am. Chem. Soc., 2004, 126: 15046-15047).

As used herein, the term "Staudinger ligation" refers to a chemical reaction developed by Saxon and Bertozzi (E. Saxon and C. Bertozzi, Science, 2000, 287: 2007-2010) that is a modification of the classical Staudinger reaction. The classical Staudinger reaction is a chemical reaction in which the combination of an azide with a phosphine or phosphite produces an aza-ylide intermediate, which upon hydrolysis yields a phosphine oxide and an amine. A Staudinger reaction is a mild method of reducing an azide to an amine; and triphenylphosphine is commonly used as the reducing agent. In a Staudinger ligation, an electrophilic trap (usually an alkyl ester) is appropriately placed on a triarylphosphine (usually in ortho to the phosphorus atom) and reacted with the azide, to yield an aza-ylide intermediate, which rearranges in aqueous media to produce a compound with amide group and a phosphine oxide function. The Staudinger ligation is so named because it ligates (attaches/covalently links) the two starting molecules together, whereas in the classical Staudinger reaction, the two products are not covalently linked after hydrolysis. The term "Staudinger ligation" also encompasses "traceless" Staudinger ligation reactions in which diarylphosphioesters or diarylphosphinothioesters are used, as described by Raines et al., J. Am. Chem. Soc., 2006, 128: 8820-8828).

The terms "labeled", "labeled with a detectable agent", and "labeled with a detectable moiety" are used herein interchangeably. When used in reference to a nucleic acid polymer, these terms specify that the nucleic acid polymer can be detected or visualized. Preferably, a label is selected such that it generates a signal which can be measured and whose intensity is related to the amount of labeled nucleic acid polymers (e.g., in a sample). In array-based detection methods of the invention, the label may desirably be selected such that it generates a localized signal, thereby allowing spatial resolution of the signal from each spot on the array. A label may be directly detectable (i.e., it does not require any further reaction or manipulation to be detectable, e.g., a fluorophore is directly detectable) or it may be indirectly detectable (i.e., it is made detectable through reaction or binding with another entity that is detectable, e.g., a hapten is detectable by immunostaining after reaction with an appropriate antibody comprising a reporter such as a fluorophore). Labels suitable for use in the present invention may be detectable by any of a variety of means including, but not limited to, spectroscopic, photochemical, biochemical, immunochemical, electrical, optical or chemical means. Suitable labels include, but are not limited to, various ligands, radionuclides, fluorescent dyes, chemiluminescent agents, microparticles, enzymes, colorimetric labels, magnetic labels, and haptens.

The terms "fluorophore", "fluorescent moiety" and "fluorescent dye" are used herein interchangeably. They refer to a molecule which, in solution and upon excitation with light of appropriate wavelength, emits light back, generally at a longer wavelength. Numerous fluorescent dyes of a wide variety of structures and characteristics are suitable for use in the practice of the present invention. In choosing a fluorophore, it is often desirable that the molecule absorbs light and emits fluorescence with high efficiency (i.e., the fluorescent molecule has a high molar extinction coefficient at the excitation wavelength and a high fluorescence quantum yield, respectively) and is photostable (i.e., the fluorescent molecule does not undergo significant degradation upon light excitation within the time necessary to perform the detection).

As used herein, the term "dual labeling" refers to a labeling process in which a nucleic acid polymer is labeled with two detectable agents that produce distinguishable signals. The nucleic acid polymer resulting from such a labeling process is said to be dually labeled. As used herein, the term "differential labeling" refers to a labeling process in which two nucleic acid polymers are labeled with two detectable agents that produce distinguishable signals (i.e., first nucleic acid polymer is labeled with a first detectable agent, a second nucleic acid polymer is labeled with a second detectable agent, and the first and second detectable agents produce distinguishable signals). The detectable agents may be of the same type (e.g., two fluorescent dyes that produce dual-color fluorescence upon excitation) or of different types (e.g., a fluorescent dye and a hapten).

The terms "cell proliferation" and "cellular proliferation" are used herein interchangeably and refer to an expansion of a population of cells by the division of single cells into daughter cells, or to the division of a single cell to daughter cells.

As used herein, the term "effective amount" refers to the amount of a substance, compound, molecule, agent or composition that elicits the relevant response in a cell, a tissue, or an organism. For example, in the case of a nucleoside administered to an organism, an effective amount of nucleoside is an amount of nucleoside that is incorporated into the DNA of cells of the organism.

As used herein, the term "organism" refers to a living system that has or can develop the ability to act or function independently. An organism may be unicellular or multicellular. Organisms include humans, animals, plants, bacteria, protozoa, and fungi.

The term "perturbation of cellular proliferation", as used herein, refers to the ability of an agent to induce (i.e., increase, enhance or otherwise exacerbate) or inhibit (i.e., decrease, slow down or otherwise suppress) cell proliferation as compared to cellular proliferation observed in the absence of the agent.

DETAILED DESCRIPTION OF CERTAIN PREFERRED EMBODIMENTS

As mentioned above, the present invention provides methods and compositions for labeling nucleic acid polymers and for measuring cellular proliferation both in vitro and in vivo. The methods of the present invention generally include a chemical reaction between a nucleotide analogue incorporated into a nucleic acid polymer and a reagent comprising a label, wherein the nucleotide analogue comprises a first reactive group and the reagent comprises a second reactive group such that the reaction between the first and second reactive groups results in labeling of the nucleic acid polymer. Any type of reaction that covalently attaches the label to the nucleotide analogue can be used in the practice of the invention. Preferred reactions are chemically inert toward biomolecules (e.g., native cellular components), can take place efficiently under biologically-relevant conditions (e.g., cell culture conditions), and involve reactive groups that are rarely found in naturally-occurring biomolecules.

In particular, the present invention provides methods of labeling nucleic acid polymers that include a [3+2] cycloaddition or a Staudinger ligation reaction between a nucleotide analogue incorporated into a nucleic acid polymer and a reagent comprising a label.

I. Labeling of Nucleic Acid Polymers Via [3+2] Cycloaddition

Figure 1B:
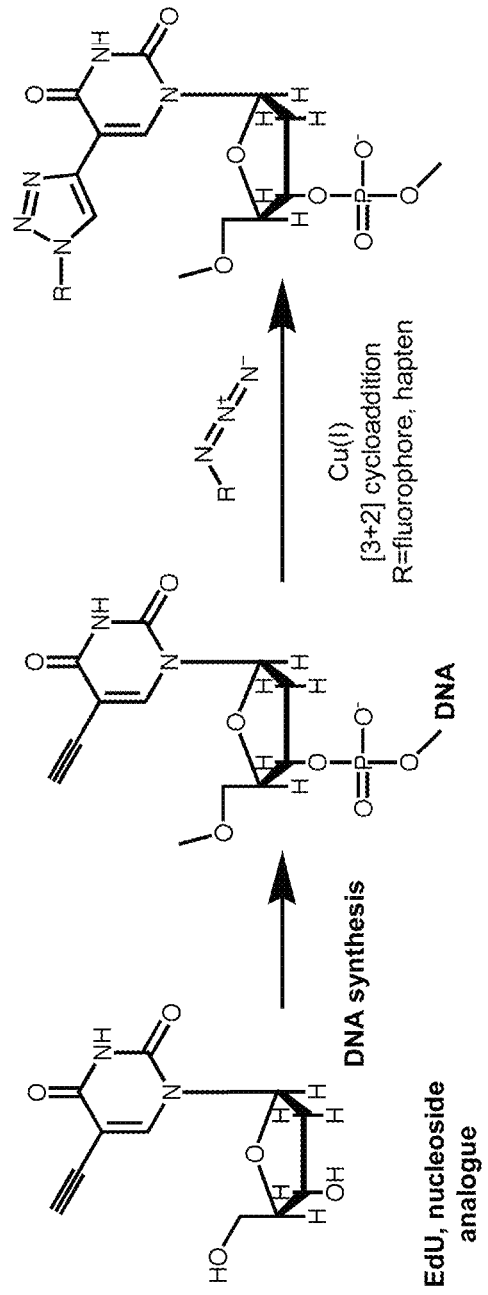

Some of the labeling methods of the present invention generally include a [3+2]cycloaddition between a first reactive unsaturated group on a nucleotide incorporated into a nucleic acid polymer and a second reactive unsaturated group attached to a label. An example of such a labeling method is schematically presented on FIG. 1 and compared to the conventional BrdU labeling method.

1. Nucleoside and Nucleotide Analogues

Nucleoside analogues (or nucleotide analogues) suitable for use in the practice of the methods of the present invention include any nucleoside analogue (or nucleotide analogue), as defined herein, that contains a reactive unsaturated group that can undergo a [3+2] cycloaddition. In some embodiments, the reactive unsaturated group is carried by the base of the nucleoside (or nucleotide). The base carrying the reactive unsaturated group can be a purine (e.g., adenine or guanine) or a pyrimidine (e.g., cytosine, uracil or thymine). In certain embodiments, the base is uracil; in some such embodiments, uracil carries the reactive unsaturated group on the 5-position. The unsaturated group can be directly or indirectly covalently attached to the base. Preferably, the unsaturated group is directly covalently attached to the base.

The reactive unsaturated group can be a 1,3-dipole such as a nitrile oxide, an azide, a diazomethane, a nitrone or a nitrile imine. In certain embodiments, the 1,3-dipole is an azide. Alternatively, the reactive unsaturated group can be a dipolarophile such as an alkene (e.g., vinyl, propylenyl, and the like) or an alkyne (e.g., ethynyl, propynyl, and the like). In certain embodiments, the dipolarophile is an alkyne, such as, for example, an ethynyl group.

Methods for the preparation of nucleoside analogues and nucleoside triphosphate analogues are known in the art. For example, procedures for the preparation of 5-substituted bases in nucleosides and nucleoside triphosphates have been developed and reported (see, for example, A. S. Jones et al., Nucleic Acids Res., 1974, 1: 105-107; R. C. Bleackley et al., Nucleic Acids Res., 1975, 2: 683-690; D. E. Bergstrom and J. L. Ruth. J. Am. Chem. Soc., 1976, 98: 1587-1589; Y. F. Shealy et al., J. Med. Chem., 1983, 26: 156-161; K. He et al., Nucleic Acids Res., 1999, 8:1788-1798; H. A. Held and S. A. Benner, Nucleic Acids Res., 2002, 30: 3857-3869).

Exemplary nucleoside analogues that may be used in the practice of the present invention include 5-ethynyl-2'deoxyuracil (also termed herein ethynyluracil or EdU) and 5-azido-2'-deoxyuracil (also termed herein azidouracil or AdU) as well as their triphosphate and phosphoramidite forms. The present Applicants synthesized EdU essentially as described by C.-S. Yu and F. Oberdorfer, Synlett, 2000, 1: 86-88; and prepared AdU using a method similar to that described in P. Sunthankar et al., Anal. Biochem., 1998, 258: 195-201 to synthesize azido-dUMP. EdU is also commercially available from Berry and Associates, Inc. (Dexter, Mich.).

2. Nucleic Acid Polymers

Nucleic acid polymers produced according to methods of the present invention or utilized in methods of the present invention are single- or double-stranded deoxyribonucleotide or ribonucleotide polymers. As will be appreciated by one of ordinary skill in the art, the nucleic acid polymers can be polynucleotides of any of a wide range of sizes including short oligonucleotides comprising at least about 8 nucleotides as well as full genomic DNA molecules.

Nucleic acid polymers containing at least one nucleotide analogue may be prepared by any of a variety of methods well known in the art including synthetic and enzymatic methods (J. Sambrook et al., "*Molecular Cloning: A Laboratory Manual*", 1989, 2$^{nd}$ Ed., Cold Spring Harbour Laboratory Press: New York, N.Y.; "*PCR Protocols: A Guide to Methods and Applications*", 1990, M. A. Innis (Ed.), Academic Press: New York, N.Y.; P. Tijssen "*Hybridization with Nucleic Acid Probes—Laboratory Techniques in Biochemistry and Molecular Biology (Parts I and II)*", 1993, Elsevier Science; "*PCR Strategies*", 1995, M. A. Innis (Ed.), Academic Press: New York, N.Y.; and "*Short Protocols in Molecular Biology*", 2002, F. M. Ausubel (Ed.), 5$^{th}$ Ed., John Wiley & Sons: Secaucus, N.J.).

For example, the inventive nucleic acid polymers may be prepared using automated, solid-phase procedure based on the phosphoramidite approach. In such a method, each nucleotide (including nucleotide analogues) is individually added to the 5'-end of the growing polynucleotide chain, which is attached at the 3'-end to a solid support. The added nucleotides are in the form of trivalent 3'-phosphoramidites that are protected from polymerization by a dimethoxytriyl (or DMT) group at the 5'-position. After base-induced phosphoramidite coupling, mild oxidation to give a pentavalent phosphotriester intermediate, DMT removal provides a new site for polynucleotide elongation. The nucleic acid polymers are then cleaved off the solid support, and the phosphodiester and exocyclic amino groups are deprotected with ammonium hydroxide. These syntheses may be performed on oligo synthesizers such as those commercially available from Perkin Elmer/Applied Biosystems, Inc (Foster City, Calif.), DuPont (Wilmington, Del.) or Milligen (Bedford, Mass.).

The inventive nucleic acid polymers can alternatively be prepared, for example using in vitro extension and/or amplification methods. Standard nucleic acid amplification methods include: polymerase chain reaction or PCR ("*PCR Protocols: A Guide to Methods and Applications*", M. A. Innis (Ed.), Academic Press: New York, 1990; and "*PCR Stratgies*", M. A. Innis (Ed.), Academic Press: New York, 1995); ligase chain reaction or LCR (U. Landegren et al., Science, 1988, 241: 1077-1080; and D. L. Barringer et al., Gene, 1990, 89: 117-122); transcription amplification (D. Y. Kwoh et al., Proc. Natl. Acad. Sci. USA, 1989, 86: 1173-1177); self-sustained sequence replication (J. C. Guatelli et al., Proc. Natl. Acad. Sci. USA, 1990, 87: 1874-1848); Q-beta replicase amplification (J. H. Smith et al., J. Clin. Microbiol. 1997, 35: 1477-1491); automated Q-beta replicase amplification assay (J. L. Burg et al., Mol. Cell. Probes, 1996, 10: 257-271) and other RNA polymerase mediated techniques such as, for example, nucleic acid sequence based amplification or NASBA (A. E. Greijer et al., J. Virol. Methods, 2001, 96: 133-147).

As will be appreciated by one of ordinary skill in the art, nucleic acid polymers of the present invention may be prepared either by a pre-synthetic modification method (i.e., incorporation of nucleotides analogues into the nucleic acid molecule) or a post-synthetic modification method (i.e., modification of naturally occurring nucleotides to nucleotide analogues in the nucleic acid molecule).

Alternatively, nucleotide analogues can be incorporated into the DNA of cells or living systems by DNA replication, or into RNA by reaction, as described below.

Isolation or purification of the nucleic acid polymers of the present invention, where necessary, may be carried out by any of a variety of methods well-known in the art. Purification of nucleic acid polymers is typically performed either by native acrylamide gel electrophoresis, by anion-exchange HPLC as described, for example by J. D. Pearson and F. E. Regnier (J. Chrom., 1983, 255: 137-149) or by reverse phase HPLC (G. D. McFarland and P. N. Borer, Nucleic Acids Res., 1979, 7: 1067-1080)

If desired, the sequence of synthetic nucleic acid polymers can be verified using any suitable sequencing method including, but not limited to, chemical degradation (A. M. Maxam and W. Gilbert, Methods of Enzymology, 1980, 65: 499-560), matrix-assisted laser desorption ionization time-of-flight (MALDI-TOF) mass spectrometry (U. Pieles et al., Nucleic Acids Res., 1993, 21: 3191-3196), mass spectrometry following alkaline phosphatase and exonuclease digestions (H. Wu and H. Aboleneen, Anal. Biochem., 2001, 290: 347-352), and the like.

3. [3+2] Cycloaddition

The methods provided herein generally include a [3+2] cycloaddition. In these methods, the [3+2] cycloaddition occurs between a first reactive unsaturated group on a nucleotide analogue incorporated into a nucleic acid polymer and a second reactive unsaturated group on a reagent comprising a label (also called herein a staining reagent).

In some embodiments of the present invention, the staining reagent is selected such that the second reactive unsaturated group can react via a [3+2] cycloaddition with the first reactive unsaturated group on the nucleotide analogue. More specifically, if the first unsaturated group is a 1,3-dipole, the second unsaturated group will be a dipolarophile that can react with the 1,3-dipole. Alternatively, if the first unsaturated group is a dipolarophile, the second unsaturated group will be a 1,3-dipole that can react with the dipolarophile.

Optimization of [3+2] cycloaddition reaction conditions is within the skill of the art. In certain preferred embodiments, the [3+2] cycloaddition is performed under aqueous conditions.

In embodiments where the 1,3-dipole is an azide and the dipolarophile is an alkyne (e.g., ethynyl group), the [3+2] cycloaddition may be performed as described by Sharpless and coworkers (V. V. Rostovtsev et al., Angew Chem., Int. Ed. Engl., 2002, 41: 1596-1599; W. G. Lewis et al., Angew Chem. Int. Ed. Engl., 2002, 41: 1053-1057; Q. Wang et al., J. Am. Chem. Soc., 2003, 125: 3192-3193) at physiological temperatures, under aqueous conditions and in the presence of copper(I) (or Cu(I)), which catalyzes the cycloaddition. This catalyzed version of the [3+2] cycloaddition is termed "click" chemistry.

In other embodiments, for example where the presence of exogenous Cu(I) is not desired (e.g., when Cu(I) is toxic to a living system), the [3+2] cycloaddition between the azide and the alkyne may be performed as described by Sharpless and coworkers except for the presence of Cu(I). In these situations, the staining reagent used in the cycloaddition comprises a Cu chelating moiety in addition to a reactive unsaturated group and a label. As used herein, the term "Cu chelating moiety" refers to any entity characterized by the presence of two or more polar groups that can participate in the formation of a complex (containing more than one coordinate bond) with copper(I) ions. A Cu chelating moiety can mobilize copper(I) ions naturally present in a living system (e.g., a cell) in the vicinity of the [3+2] cycloaddition. Specific Cu(I) chelators are known in the art and include, but are not limited to, neocuproine (H. H. Al-Sa'doni et al., Br. J. Pharmacol., 1997, 121: 1047-1050; J. G. De Man et al., Eur. J. Pharmacol., 1999, 381: 151-159; C. Gocmen et al., Eur. J. Pharmacol., 2000, 406: 293-300) and bathocuproine disulphonate (M. Bagnati et al., Biochem. Biophys. Res. Commun., 1998, 253: 235-240).

4. Labels and Detection of Labeled Nucleic Acid Polymers

The methods of the present invention include a [3+2] cycloaddition between a first reactive unsaturated group on a nucleotide analogue incorporated into a nucleic acid polymer and a second reactive unsaturated group attached to a label. The [3+2] cycloaddition reaction results in labeling of the nucleic aid polymer.

A. Labels

As already mentioned above, the role of a label is to allow visualization or detection of a nucleic acid polymer, e.g., DNA in a cell, following labeling. Preferably, a label (or detectable agent or moiety) is selected such that it generates a signal which can be measured and whose intensity is related (e.g., proportional) to the amount of labeled nucleic acid polymer, e.g., in a sample being analyzed. In array-based detection methods of the invention (see below), the detectable agent is also preferably selected such that it generates a localized signal, thereby allowing spatial resolution of the signal for each spot on the array.

The association between the label and the staining reagent comprising the second reactive unsaturated group is preferably covalent. A label can be directly attached to the unsaturated group on the staining reagent or indirectly through a linker.

Methods for attaching detectable moieties to chemical molecules are well-known in the art. In certain embodiments, the label and unsaturated group are directly, covalently linked to each other. The direct covalent binding can be through an amide, ester, carbon-carbon, disulfide, carbamate, ether, thioether, urea, amine, or carbonate linkage. The covalent binding can be achieved by taking advantage of functional groups present on the unsaturated group and detectable moiety. Suitable functional groups that can be used to attach the two chemical entities together include, but are not limited to, amines, anhydrides, hydroxy groups, carboxy groups, and thiols. A direct linkage may also be formed using an activating agent, such as a carbodiimide. A wide range of activating agents are known in the art and are suitable for linking a label and an unsaturated group.

In other embodiments, the unsaturated group of the staining reagent and the label are indirectly covalently linked to each other via a linker group. This can be accomplished by using any number of stable bifunctional agents well known in the art, including homofunctional and heterofunctional linkers (see, for example, Pierce Catalog and Handbook). The use of a bifunctional linker differs from the use of an activating agent in that the former results in a linking moiety being present in the reaction product, whereas the latter results in a direct coupling between the two moieties involved in the reaction. The role of the bifunctional linker may be to allow the reaction between two otherwise inert moieties. Alternatively or additionally, the bifunctional linker, which becomes part of the reaction product, may be selected such that it confers some degree of conformational flexibility to the reaction product, or other useful or desired properties. In certain embodiments, the linker is cleavable (e.g., chemically cleavable or photochemically cleavable). The presence of a cleavable linker between the label and the nucleotide analogue allows for temporary labeling of the nucleic acid polymer. With such a system, whenever desired (e.g., following detection of the nucleic acid polymer), the label can be cleaved off the nucleotide analogue to which it is attached. Cleavable linkers are known in the art. For example, the linker may be a cystamine linker, the disulfide bond of which can be reduced using dithiothreitol (DTT) (see Example 8).

Any of a wide variety of labeling/detectable agents can be used in the practice of the present invention. Suitable detectable agents include, but are not limited to, various ligands, radionuclides (such as, for example, $^{32}P$, $^{35}S$, $^{3}H$, $^{14}C$, $^{125}I$, $^{131}I$, and the like); fluorescent dyes (for specific exemplary fluorescent dyes, see below); chemiluminescent agents (such as, for example, acridinium esters, stabilized dioxetanes, and the like); spectrally resolvable inorganic fluorescent semiconductor nanocrystals (i.e., quantum dots), metal nanoparticles (e.g., gold, silver, copper and platinum) or nanoclusters; enzymes (such as, for example, those used in an ELISA, i.e., horseradish peroxidase, beta-galactosidase, luciferase, alkaline phosphatase); colorimetric labels (such as, for example, dyes, colloidal gold, and the like); magnetic labels (such as, for example, Dynabeads™); and biotin, dioxigenin, haptens, and proteins for which antisera or monoclonal antibodies are available.

In certain embodiments, the label comprises a fluorescent moiety. Numerous known fluorescent labeling moieties of a wide variety of chemical structures and physical characteristics are suitable for use in the practice of the present invention. Suitable fluorescent dyes include, but are not limited to, fluorescein and fluorescein dyes (e.g., fluorescein isothiocyanine or FITC, naphthofluorescein, 4',5'-dichloro-2',7-dimethoxy-fluorescein, 6-carboxyfluorescein or FAM), carbocyanine, merocyanine, styryl dyes, oxonol dyes, phycoerythrin, erythrosin, eosin, rhodamine dyes (e.g., carboxytetramethylrhodamine or TAMRA, carboxyrhodamine 60, carboxy-X-rhodamine (ROX), lissamine rhodamine B, rhodamine 6G, rhodamine Green, rhodamine Red, tetramethylrhodamine or TMR), coumarin and coumarin dyes (e.g., methoxycoumarin, dialkylaminocoumarin, hydroxycoumarin and aminomethylcoumarin or AMCA), Oregon Green Dyes (e.g., Oregon Green 488, Oregon Green 500, Oregon Green 514), Texas Red, Texas Red-X, Spectrum Red™, Spectrum Green™, cyanine dyes (e.g., Cy-3™, Cy-5™, Cy-3.5™, Cy-5.5™), Alexa Fluor dyes (e.g., Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), BODIPY dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), IRDyes (e.g., IRD40, IRD 700, IRD 800), and the like. For more examples of suitable fluorescent dyes and methods for coupling fluorescent dyes to other chemical entities see, for example, "*The Handbook of Fluorescent Probes and Research Products*", 9*th* Ed., Molecular Probes, Inc., Eugene, Oreg.

Favorable properties of fluorescent labeling agents to be used in the practice of the invention include high molar absorption coefficient, high fluorescence quantum yield, and photostability. In certain embodiments, labeling fluorophores desirably exhibit absorption and emission wavelengths in the visible (i.e., between 400 and 750 nm) rather than in the ultraviolet range of the spectrum (i.e., lower than 400 nm). Other desirable properties of the fluorescent moiety may include cell permeability and low toxicity, for example if labeling of the nucleic acid polymer is to be performed in a cell or an organism (e.g., a living animal).

As reported in the Examples, various fluorescent staining reagents have been used by the present Applicants, including XRhodamine-azide and Alexa568-azide, which are non-cell permeable, and tetramethylrhodamine (TMR)-azide, which is cell permeable.

Figure 2:
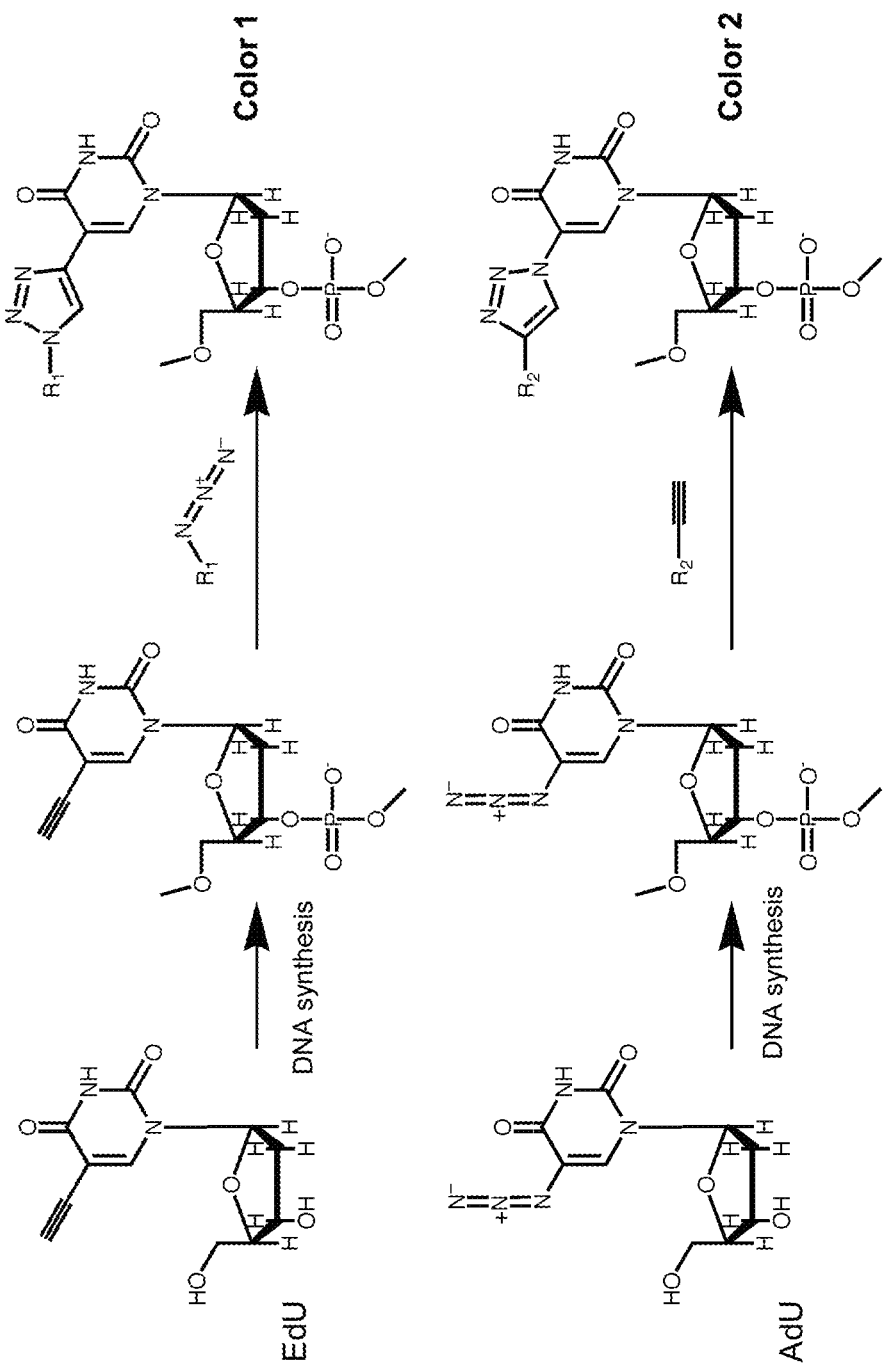
FIG. 2 presents a scheme showing an example of 2-color DNA labeling according to the present invention.

The present invention also provides for two-color labeling of nucleic acid polymers (see FIG. 2). For example, according to the present invention, two or more different labels may be incorporated into a single nucleic acid polymer. In some embodiments, such incorporation is achieved via two [3+2] cycloaddition reactions: a first cycloaddition takes place between a first reactive unsaturated group on a nucleotide analogue incorporated into a first nucleic acid polymer and a second reactive unsaturated group on a first reagent attached to a first label; a second cycloaddition takes place between a third reactive unsaturated group on a nucleotide analogue incorporated into a second nucleic acid polymer and a fourth reactive unsaturated group on a second reagent attached to a second label. The first and second nucleic acid polymers may be the same molecule (e.g., dual labeling of DNA in a cell) or different/individual molecules (e.g., differential labeling of DNA from two different cells, cell populations or cell samples). The first and second labels are preferably selected such that they produce distinguishable detectable signals.

In certain two-label embodiments, the first and second detectable agents or labels are fluorescent dyes. To allow for two-color detection, the first and second fluorescent labels may desirably constitute a matched pair that is compatible with the detection system to be used. Matched pairs of fluorescent labeling dyes typically produce signals that are spectrally distinguishable. For example, in some embodiments, the fluorescent dyes in a matched pair do not significantly absorb light in the same spectral range (i.e., they exhibit different absorption maxima wavelengths) and can be excited (for example, sequentially) using two different wavelengths. Alternatively, the fluorescent dyes in a matched pair may emit light in different spectral ranges (i.e., they produce a dual-color fluorescence upon excitation).

Pairs of fluorescent labels are known in the art (see, for example, R. P. Haugland, "*Molecular Probes: Handbook of Fluorescent Probes and Research Chemicals 1992-1994*", 5$^{th}$ Ed., 1994, Molecular Probes, Inc.). Exemplary pairs of fluorescent dyes include, but are not limited to, rhodamine and fluorescein (see, for example, J. DeRisi et al., Nature Gen., 1996, 14: 458-460); Spectrum Red™ and Spectrum Green™ (commercially available from Vysis, Inc., Downers Grove, Ill.); and Cy-3™ and Cy-5™ (commercially available from Amersham Life Sciences, Arlington Heights, Ill.).

The selection of a particular label (or set of labels) will depend on the purpose of the labeling to be performed and will be governed by several factors, such as the ease and cost of the labeling method, the quality of sample labeling desired, the effects of the detectable moiety on the cell or organism, the nature of the detection system, the nature and intensity of the signal generated by the detectable moiety, and the like.

B. Detection of Labeled Nucleic Acid Polymers

As will be recognized by one of ordinary skill in the art, detection of nucleic acid polymers labeled according to methods disclosed herein may be performed by any of a wide variety of methods, and using any of a wide variety of techniques. Selection of a suitable detection method and/or detection technique based on the nature of the label (e.g., radionuclide, fluorophore, chemiluminescent agent, quantum dot, enzyme, magnetic label, hapten, etc) is within the skill in the art.

For example, fluorescently labeled nucleic acid polymers may be detected using fluorescence detection techniques, including, but not limited to, flow cytometry and fluorescence microscopy. Selection of a specific fluorescence detection technique will be governed by many factors including the purpose of the labeling experiment (e.g., study of chromosomes ultrastructure, cell proliferation determination, or toxicity assay) as well as the location of the labeled nucleic acid polymer to be detected (i.e., such as inside a living cell or inside a tissue).

Flow cytometry is a sensitive and quantitative technique that analyzes particles (such as cells) in a fluid medium based on the particles' optical characteristic (H. M. Shapiro, "*Practical Flow Cytometry*", 3$^{rd}$ Ed., 1995, Alan R. Liss, Inc.; and "*Flow Cytometry and Sorting, Second Edition*", Melamed et al. (Eds), 1990, Wiley-Liss: New York). A flow cytometer hydrodynamically focuses a fluid suspension of particles containing one or more fluorophores, into a thin stream so that the particles flow down the stream in a substantially single file and pass through an examination or analysis zone. A focused light beam, such as a laser beam, illuminates the particles as they flow through the examination zone, and optical detectors measure certain characteristics of the light as it interacts with the particles (e.g., light scatter and particle fluorescence at one or more wavelengths).

Alternatively or additionally, fluorescently labeled nucleic acid polymers in cells, tissues or organisms may be visualized and detected by fluorescence microscopy using different imaging techniques. In addition to conventional fluorescence microscopy, fluorescently labeled nucleic acid polymers can be analyzed by, for example, time-lapse fluorescence microscopy, confocal fluorescence microscopy, or two-photon fluorescence microscopy. Time-lapse microscopy techniques (D. J. Stephens and V. J. Allan, Science, 2003, 300: 82-86) can provide a complete picture of complex cellular processes that occur in three dimensions over time. Information acquired by these methods allow dynamic phenomena such as cell growth, cell motion and cell nuclei division to be monitored and analyzed quantitatively. Confocal microscopy (L. Harvath, Methods Mol. Biol., 1999, 115: 149-158; Z. Foldes-Papp et al., Int. Immunopharmacol., 2003, 3: 1715-1729) offers several advantages over conventional optical microscopy, including controllable depth of field, the elimination of image degrading out-of-focus information, and the ability to collect serial optical sections from thick specimens (e.g., tissues or animals). Two-photon fluorescence microscopy (P. T. So et al., Annu. Rev. Biomed. Eng., 2000, 2; 399-429), which involves simultaneous absorption of two photons by the fluorophore at the focal point of the microscope, allows three-dimensional imaging in highly localized volumes (e.g., in the nucleus of cells) with minimal photobleaching and photodamage.

Signals from fluorescently labeled nucleic acid polymers attached to microarrays or located inside cells in multi-well plates can be detected and quantified by any of a variety of automated and/or high-throughput instrumentation systems including fluorescence multi-well plate readers, fluorescence activated cell sorters (FACS) and automated cell-based imaging systems that provide spatial resolution of the signal. Methods for the simultaneous detection of multiple fluorescent labels and the creation of composite fluorescence images are well-known in the art and include the use of "array reading" or "scanning" systems, such as charge-coupled devices (i.e., CCDs) (see, for example, Y. Hiraoka et al., Science, 1987, 238: 36-41; R. S. Aikens et al., Meth. Cell Biol. 1989, 29: 291-313; A. Divane et al., Prenat. Diagn. 1994, 14: 1061-1069; S. M. Jalal et al., Mayo Clin. Proc. 1998, 73: 132-137; V. G. Cheung et al., Nature Genet. 1999, 21: 15-19; see also, for example, U.S. Pat. Nos. 5,539,517; 5,790,727; 5,846,708; 5,880,473; 5,922,617; 5,943,129; 6,049,380; 6,054,279; 6,055,325; 6,066,459; 6,140,044; 6,143,495; 6,191,425; 6,252,664; 6,261,776; and 6,294,331). A variety of instrumentation systems have been developed to automate such analyses including the automated fluorescence imaging and automated microscopy systems developed by Cellomics, Inc. (Pittsburgh, Pa.), Amersham Biosciences (Piscataway, N.J.), TTP LabTech Ltd (Royston. UK), Quantitative 3 Dimensional Microscopy (Q3DM) (San Diego, Calif.), Evotec AG (Hamburg, Germany), Molecular Devices Corp. (Sunnyvale, Calif.), and Carl Zeiss AG (Oberkochen, Germany).

Figure 3:
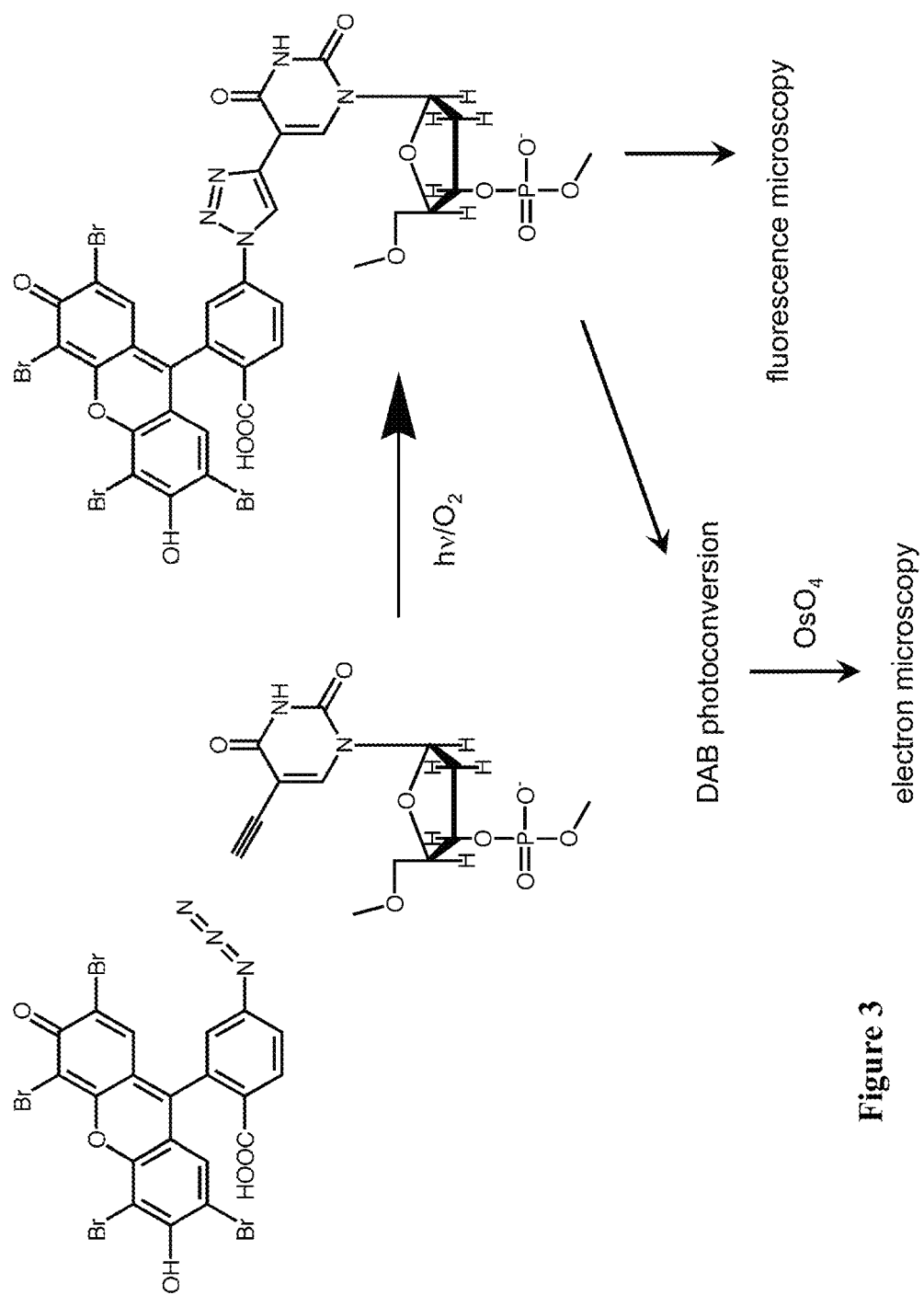
FIG. 3 presents a scheme showing an example of DAB photoconversion according to the present invention.

The fluorescent signal from labeled nucleic acid polymers within a cell or a tissue can also be visualized after DAB (diaminobenzidine) photoconversion (as shown on FIG. 3). Photoconversion is the process by which a fluorescent probe (e.g., within a cell) is converted into an electron-dense probe, labeling the area or structure of interest for study at light and electron microscope levels. The principle of photoconverting fluorescent dyes to an insoluble light and electron-dense diaminobenzidine (DAB) reaction product was first demonstrated by A. R. Maranto (Science, 1982, 217: 953-955). DAB photoconversion is generally accomplished by incubating the fluorescently labeled cells with or bathing the fluorescently labeled tissue in a DAB solution while exposing the cells or tissue to a frequency of light that maximally excites the fluorophore.

A diaminobenzidine stain may have several advantages over a fluorescent stain due to its greater stability and greater density A diaminobenzidine stain can also be intensified by employing osmium tetroxide and potassium ferrocyanide following the DAB treatment (H. C. Mutasa, Biotech. Histochem., 1995, 70: 194-201). Examples of fluorophores that have been reported to undergo efficient DAB conversion include, but are not limited to, 4,6-diamidino-2-phenylindole (DAPI), Fast Blue, Lucifer Yellow, Diamidino Yellow, Evans Blue, acridine orange, ethidium bromide, 5,7-dihydroxytryptamine, 1,1'-dioctadecyl-3,3,3',3'-tetramethyl-indolcarbocyanine perchlorate, 3,3'-dioctadecylindocarbocyanine (DiI), rhodamine-123, and propidium iodide.

Before DAB photoconversion, fluorescently labeled nucleic acid polymers in cells or tissue may be detected and localized by fluorescence microscopy. After DAB conversion, the nucleic acid polymers may be visualized by transmission electron microscopy.

C. Signal-to-Noise Ratio Improvements

In another aspect, the present invention provides a system for improving the signal-to-noise ratio in the detection of a nucleic acid polymer labeled with a fluorescent moiety using a labeling process disclosed herein.

Figure 4:
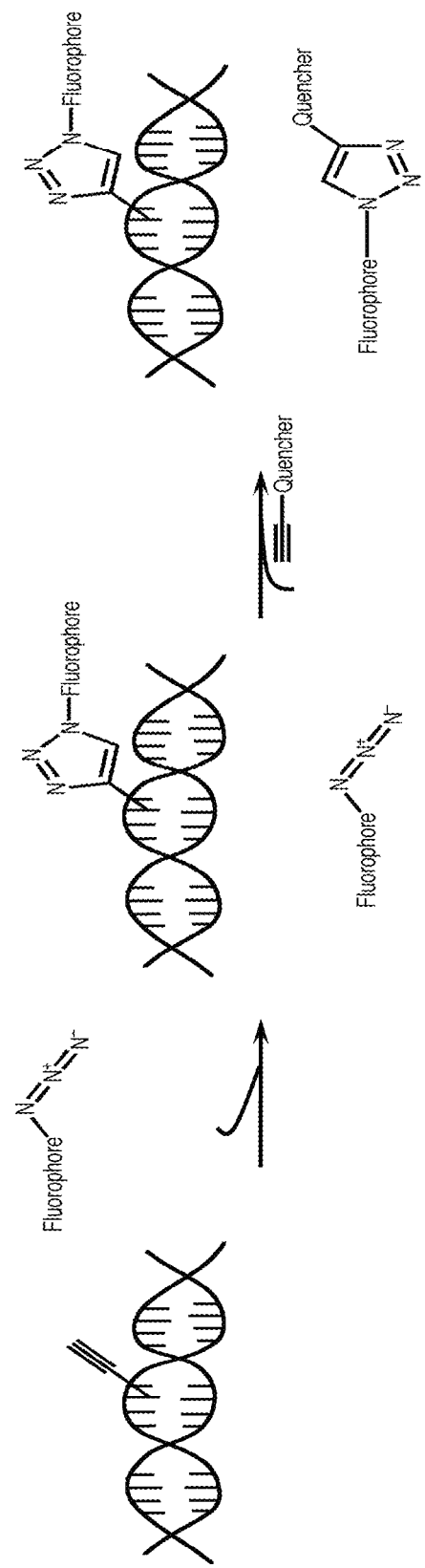
FIG. 4 presents a scheme illustrating a method of the present invention for quenching non-specific (i.e., background) signal from unreacted staining reagent (i.e., the flurophore-azide).

Any molecule of staining reagent that has not been consumed by the [3+2]cycloaddition labeling reaction may contribute to the background (i.e., non-specific) signal. The present invention provides a strategy for reducing or eliminating this background signal which comprises quenching the fluorescent signal of the label on the unreacted staining reagent by reaction with a molecule comprising a quencher moiety. For example, in some embodiments, the reaction between the reagent and the molecule comprising the quencher moiety is a [3+2]cycloaddition (as shown on FIG. 4).

Thus, certain inventive methods for improving the signal-to-noise ratio in detection of a fluorescently labeled nucleic acid polymer prepared as described herein, comprise contacting unreacted reagent comprising a second reactive unsaturated group and a fluorescent label (and optionally a Cu chelating moiety) with a quenching molecule comprising a reactive unsaturated group attached to a quenching moiety such that a [3+2] cycloaddition takes place between the reactive unsaturated groups of the staining reagent and quenching molecule. After reaction, the physical proximity between the fluorescent label and the quenching moiety prevents detection of a fluorescent signal from the fluorescent label.

Examples of quenching moieties include, but are not limited to DABCYL (i.e., 4-(4'-dimethylaminophenylazo)-benzoic acid) succinimidyl ester, diarylrhodamine carboxylic acid, succinimidyl ester (or QSY-7), and 4',5'-dinitrofluorescein carboxylic acid, succinimidyl ester (or QSY-33) (all available, for example, from Molecular Probes), quencher1 (QI; available from Epoch Biosciences, Bothell, Wash.), or "Black hole quenchers" BHQ-1, BHQ-2, and BHQ-3 (available from BioSearch Technologies, Inc., Novato, Calif.).

5. Labeling of Nucleic Acid Polymers in Cells

The present invention also provides methods for labeling nucleic acid polymers in cells. Such methods comprise: contacting a cell with an effective amount of a nucleoside analogue that comprises a first reactive unsaturated group such that the nucleoside analogue is incorporated into DNA of the cell; contacting the cell with a reagent comprising a second reactive unsaturated group attached to a label such that a [3+2] cycloaddition occurs between the first and second reactive unsaturated groups.

Unless otherwise stated, the staining reagent and [3+2] cycloaddition conditions used in these methods are analogous to those described above for the methods of labeling nucleic acid polymers. As already mentioned above, the labeling methods of the present invention exhibit several advantages over currently available labeling protocols including the possibility of staining nucleic acid polymers in living cells. The terms "living cell" and "live cell" are used herein interchangeably and refer to a cell which is considered living according to standard criteria for that particular type of cell, such as maintenance of normal membrane potential, energy metabolism, or proliferative capability. In particular, the methods of the present invention do not require fixation and/or denaturation of the cells.

A. Cells

In some embodiments, the invention relates to incorporation of labels into nucleic acid polymers in cells in culture. In certain embodiments, the cells are grown in standard tissue culture plastic ware. Such cells include normal and transformed cells derived. In certain embodiments, cells are of mammalian (human or animal, such as rodent or simian) origin. Mammalian cells may be of any fluid, organ or tissue origin (e.g., blood, brain, liver, lung, heart, bone, and the like) and of any cell types (e.g., basal cells, epithelial cells, platelets, lymphocytes, T-cells, B-cells, natural killer cells, macrophages, tumor cells, and the like).

Cells suitable for use in the methods of the present invention may be primary cells, secondary cells or immortalized cells (i.e., established cell lines). They may have been prepared by techniques well-known in the art (for example, cells may be obtained by drawing blood from a patient or a healthy donor) or purchased from immunological and microbiological commercial resources (for example, from the American Type Culture Collection. Manassas, Va.). Alternatively or additionally, cells may be genetically engineered to contain, for example, a gene of interest such as a gene expressing a growth factor or a receptor.

Cells to be used in the methods of the present invention may be cultured according to standard culture techniques. For example, cells are often grown in a suitable vessel in a sterile environment at 37° C. in an incubator containing a humidified 95% air-5% $CO_2$ atmosphere. Vessels may contain stirred or stationary cultures. Various cell culture media may be used including media containing undefined biological fluids such as fetal calf serum. Cell culture techniques are well known in the art, and established protocols are available for the culture of diverse cell types (see, for example, R. I. Freshney, "*Culture of Animal Cells: A Manual of Basic Technique*", $2^{nd}$ Edition, 1987, Alan R. Liss, Inc.).

B. Incorporation of Nucleoside Analogue by DNA Replication

Incorporation of nucleoside analogues into DNA by DNA replication is a process well-known in the art. In general, nucleoside analogues are transported across the cell membrane by nucleoside transporters and are phosphorylated in cells by kinases to their triphosphate forms. The nucleoside analogue triphosphates then compete with the naturally-occurring deoxyribonucleotides as substrates of cellular DNA polymerases. Such a process is used for the incorporation of $^3$H-thymidine and 5'-bromo-2'-deoxyuridine (BrdU) into DNA for labeling purposes as well as in cancer therapy (D. Kufe et al., Blood, 1984, 64: 54-58; E. Beutler, Lancet, 1992, 340: 952-956; Y. F. Hui and J. Reitz, Am. J. Health-Syst. Pharm., 1997, 54: 162-170; H. Iwasaki et al., Blood, 1997, 90: 270-278) and in the treatment of human immunodeficiency virus infection (J. Balzarini, Pharm. World Sci., 1994, 16: 113-126).

Contacting the cells in vitro with an effective amount of a nucleoside analogue such that the nucleoside analogue is incorporated into DNA of the cell may be carried out using any suitable protocol. In certain preferred embodiments, the nucleoside analogue is incorporated into DNA using exponentially growing cells or cells in the S-phase of the cell cycle (i.e., the synthesis phase). If desired, cells may be synchronized in early S-phase by serum deprivation before the labeling-pulse procedure.

The step of contacting a cell with an effective amount of a nucleoside analogue may be performed, for example, by incubating the cell with the nucleoside analogue under suitable incubation conditions (e.g., in culture medium at 37° C. as described in Example 1). In certain situations, it may be desirable to avoid disturbing the cells in any way (e.g., by centrifugation steps or temperature changes) that may perturb their normal cell cycling patterns. The incubation time will be dependent on the cell population's rate of cell cycling entry and progression. Optimization of incubation time and conditions is within the skill in the art.

C. [3+2] Cycloaddition in Cells

Following incorporation of the nucleotide analogue into the DNA of in vitro cells, the step of contacting the cells with a staining reagent comprising the second reactive unsaturated group and a label may be performed by any suitable method. In some embodiments, the cells are incubated in the presence of the staining reagent in a suitable incubation medium (e.g., culture medium) at 37° C. and for a time sufficient for the reagent to penetrate into the cell and react with any nucleotide analogue incorporated into the DNA of the cells. Optimization of the concentration of staining reagent, cycloaddition reaction time and conditions is within the skill in the art.

As already mentioned above, in embodiments where the presence of exogenous Cu(I) is not desirable, the [3+2] cycloaddition may be carried out using a staining reagent that comprises the second reactive unsaturated group, a label, and a Cu(I) chelating moiety.

In embodiments where the staining reagent does not exhibit high cell permeability, permeabilization may be performed to facilitate access of the staining reagent to cellular cytoplasm, or intracellular components or structures of the cells. In particular, permeabilization may allow a reagent to enter into a cell and reach a concentration within the cell that is greater than that which would normally penetrate into the cell in the absence of such permeabilization treatment.

Permeabilization of the cells may be performed by any suitable method (see, for example, C. A. Goncalves et al., Neurochem. Res. 2000, 25: 885-894). Such methods include, but are not limited to, exposure to a detergent (such as CHAPS, cholic acid, deoxycholic acid, digitonin, n-dodecyl-j3-D-maltoside, lauryl sulfate, glycodeoxycholic acid, n-lauroylsarcosine, saponin, and triton X-100) or to an organic alcohol (such as methanol and ethanol). Other permeabilization methods comprise the use of certain peptides or toxins that render membranes permeable (see, for example, O. Aguilera et al., FEBS Lett. 1999, 462: 273-277; A. Bussing et al., Cytometry, 1999, 37: 133-139). Selection of an appropriate permeabilizing agent and optimization of the incubation conditions and time can easily be performed by one of ordinary skill in the art.

As described in Example 2, the present Applicants have incubated HeLa cells in the presence or absence of EdU, permeabilized the cells, and stained them with Xrhodamine-azide. Fluorescence images of the two cell populations are presented on FIG. 5. This figure illustrates the efficiency of the inventive labeling methods in vitro. Furthermore, detection of labeled DNA in living cells using such methods was found to be complete within minutes (see FIG. 6 and FIG. 7). Applicants have also incubated HeLa cells in the presence of AdU, and stained them with Alexa568-alkyne (see Example 7). Fluorescence images of cell populations thus treated are presented on FIG. 16.

6. Labeling of Nucleic Acid Polymers in Tissues or Organisms

The present invention also provides methods for labeling nucleic acid polymers in organisms (i.e., living biological systems). Such methods comprise steps of: administering to an organism an effective amount of a nucleoside analogue that comprises a first reactive unsaturated group such that the nucleoside analogue is incorporated into the DNA in cells of the organism; contacting at least one cell of the organism with a reagent comprising a second reactive unsaturated group attached to a label such that a [3+2] cycloaddition occurs between the first and second reactive unsaturated groups.

Unless otherwise stated, the staining reagents and [3+2] cycloaddition conditions used in these methods are analogous to those described above for the methods of labeling nucleic acid polymers in cells and can easily be determined/optimized by one skilled in the art.

A. Organisms

Methods of labeling of the present invention may be performed using any living system that has or can develop the ability to act or function independently. Thus, labeling methods of the present invention may be performed in unicellular or multicellular systems, including, humans, animals, plants, bacteria, protozoa, and fungi. In certain preferred embodiments, the labeling methods of the present invention are performed in a human or another mammal (e.g., mouse, rat, rabbit, dog, cat, cattle, swine, sheep, horse or primate).

B. Incorporation of Nucleoside Analogues by DNA Replication in Living Systems

Administration of a nucleoside analogue to an organism may be performed using any suitable method that results in incorporation of the nucleoside analogue into the DNA of cells of the organism.

For example, the nucleoside analogue may be formulated in accordance with conventional methods in the art using a physiologically and clinically acceptable solution. Proper solution is dependent upon the route of administration chosen. Suitable routes of administration can, for example, include oral, rectal, transmucosal, transcutaneous, or intestinal administration; parenteral delivery, including intramuscular, subcutaneous, intramedullary injections, as well as intrathecal, direct intraventricular, intravenous, intraperitoneal, intranasal, or intraocular injections. Alternatively, the nucleoside analogue preparation can be administered in a local rather than systemic manner, for example, via injection directly into a specific tissue, often in a depot or sustained release formulation.

C. [3+2] Cycloaddition

Following incorporation of the nucleotide analogue into the DNA of cells of the organism, the step of contacting at least one cell of the organism with a reagent comprising the second reactive unsaturated group attached to a label may be performed by any suitable method that allows for the [3+2] cycloaddition to take place.

In certain embodiments, cells are collected (e.g., by drawing blood from the organism), isolated from a tissue obtained by biopsy (e.g., needle biopsy, laser capture micro dissection or incisional biopsy) or isolated from an organ or part of an organ (e.g., harvested at autopsy). The cells can then be submitted to the [3+2] cycloaddition staining as described above.

In other embodiments, a tissue obtained by biopsy or an organ or part of an organ harvested at autopsy may be prepared for staining as known in the art (e.g., fixed, embedded in paraffin and sectioned) and incubated in the presence of the [3+2] cycloaddition reagent (e.g., after de-waxing).

Example 4 describes an experiment carried out by the present Applicants where mice were intraperitoneally injected with EdU and their organs harvested 3 days after injection, prepared for staining and stained with Xrhodamine-azide and with Hoechst (a fluorescent dye specific for DNA staining). Fluorescence images of the intestine and of the brain of these mice are presented on FIGS. 8 and 9, and FIG. 10, respectively.

7. Isolated Labeled Nucleic Add Polymers

In another aspect, the present invention provides isolated detectable nucleic acid polymers, for example prepared by one of the methods described herein. More specifically, the present invention provides nucleic acid polymers that are detectable following a [3+2]cycloaddition reaction as well as isolated nucleic acid polymers that contain at least one detectable moiety that has been incorporated via a [3+2] cycloaddition.

In certain embodiments, an inventive nucleic acid polymer contains at least one nucleotide analogue comprising a reactive unsaturated group. Preferably, the reactive unsaturated group can undergo a [3+2] cycloaddition in the presence of a reagent comprising a different reactive unsaturated group attached to a label.

In other embodiments, an inventive nucleic acid polymer contains at least one nucleotide analogue attached to a label. For example, the nucleotide analogue may comprise a cycloadduct resulting from a [3+2] cycloaddition.

In still other embodiments, an inventive nucleic acid polymer contains at least one first nucleotide analogue comprising a first unsaturated group and at least one second nucleotide analogue comprising a second reactive unsaturated group. The first reactive unsaturated group can generally undergo a [3+2] cycloaddition in the presence of a first reagent comprising a third reactive unsaturated group attached to a first label, and the second reactive unsaturated group can generally undergo a [3+2] cycloaddition in the presence of a second reagent comprising a fourth reactive unsaturated group attached to a second label.

In yet other embodiments, an inventive nucleic acid polymer contains at least one first nucleotide analogue attached to a first label and at least one second nucleotide analogue attached to a second label. Preferably, the first nucleotide analogue comprises a cycloadduct resulting from a first [3+2] cycloaddition, and the second nucleotide analogue comprises a cycloadduct resulting from a second [3+2] cycloaddition.

The detectable nucleic acid polymers of the present invention may be prepared by any suitable method, as described herein, including synthetic methods and enzymatic methods (e.g., by reverse transcription of total RNA).

As can be appreciated by one of ordinary skill in the art, the isolated detectable nucleic acid polymers of the present invention may be used in a wide variety of applications.

For example, they may be used as detection probes in hybridization assays, including microarray-based hybridization assays. In such applications, the detectable nucleic acid polymers are preferably oligonucleotides (i.e., short stretches of nucleic acid sequences). Oligonucleotides used in hybridization assays generally comprise between about 5 and about 150 nucleotides, for example between about 15 and about 100 nucleotides or between about 15 and about 50 nucleotides. The detectable nucleic acid polymers provided by the present invention may be used to contact an array or microarray in a hybridization assay. In such embodiments, the detectable nucleic acid probes may be provided with appropriate staining reagents. Alternatively, the detectable nucleic acid polymers are provided attached to an array or microarray for a hybridization assay.

Arrays according to the present invention comprise a plurality of detectable nucleic acid polymers immobilized to discrete spots on a substrate surface. Substrate surfaces can be made of any of rigid, semi-rigid or flexible materials that allow for direct or indirect attachment (i.e., immobilization) of detectable nucleic acid polymers to the substrate surface. Suitable materials include, but are not limited to, cellulose, cellulose acetate, nitrocellulose, glass, quartz other crystalline substrates such as silicones, and various plastics and plastic copolymers. When fluorescence is to be detected, arrays comprising cyclo-olefin polymers may preferably be used.

The presence of reactive functional chemical groups on the materials can be exploited to directly or indirectly attach the detectable nucleic acid polymers to the substrate surface. Methods for immobilizing oligonucleotides to substrate surfaces to form an array are well-known in the art.

8. Cells Comprising Detectable Nucleic Acid Polymers

In another aspect, the present invention provides cells comprising detectable nucleic acid polymers, for example prepared by one or more of the methods described herein. More specifically, the present invention provides cells comprising nucleic acid polymers that are detectable following a [3+2] cycloaddition reaction as well as cells comprising nucleic acid polymers that contain at least one detectable moiety that has been incorporated via a [3+2]cycloaddition. As will be recognized by one of ordinary skill in the art, a cell of the invention may comprise any of the detectable nucleic acid polymers described herein.

II. Labeling of Nucleic Acid Polymers Via Staudinger Ligation

Figures 18A, 18B:
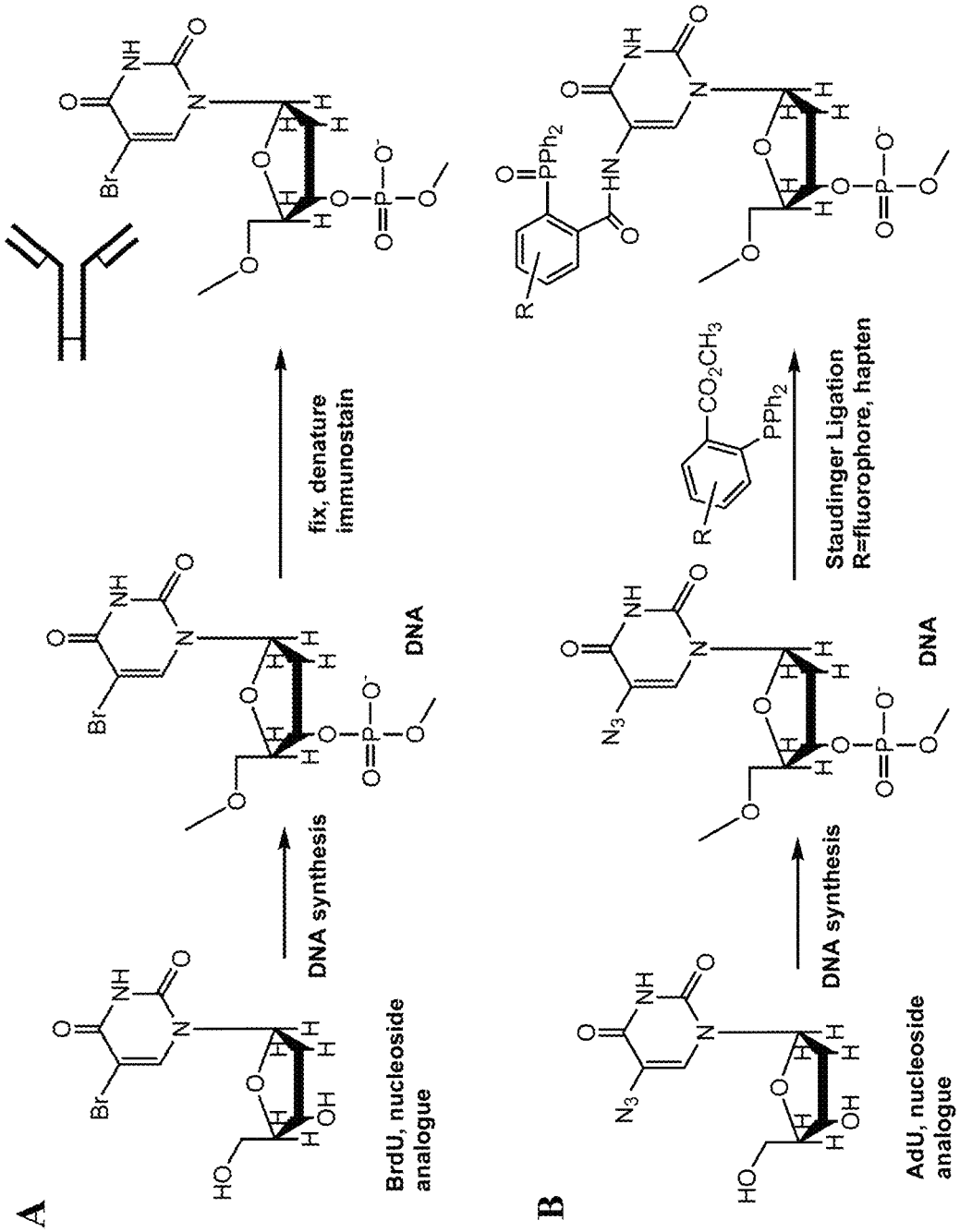
FIG. 18 presents two schemes showing (A) DNA labeling using BrdU as known in the art, and (B) DNA labeling using a method of the present invention that includes incorporation of the nucleoside analogue AdU (i.e., azido-dU) into DNA by DNA replication followed by Staudinger ligation between the azide group and the triarylphosphine of the labeling reagent.

Some of the labeling methods of the present invention generally include a Staudinger ligation between an azide group on a nucleotide incorporated into a nucleic acid polymer and a substituted triarylphosphine attached to a label. An example of such a labeling method is schematically presented on FIG. 18 and compared to the conventional BrdU labeling method.

1. Nucleoside and Nucleotide Analogues

Nucleoside analogues (or nucleotide analogues) suitable for use in the practice of these methods include any nucleoside analogue (or nucleotide analogue), as defined herein, that comprises an azide group. In some embodiments, the azide group is carried by the base of the nucleoside (or nucleotide). The base carrying the azide group can be a purine (e.g., adenine or guanine) or a pyrimidine (e.g., cytosine, uracil or thymine). In certain embodiments, the base is uracil; in some such embodiments, uracil may carry the azide group on the 5-position. The azide group can be directly or indirectly covalently attached to the base. Preferably, the azide group is directly covalently attached to the base.

Exemplary nucleoside analogues that may be used in the practice of the present invention include 5-azido-2'-deoxyuracil (also termed herein azidouracil) as well as its triphosphate and phosphoramidite forms. The present Applicants prepared 5-azido-2'-deoxyuridine (AdU) using a method similar to that described in P. Sunthankar et al., Anal. Biochem., 1998, 258: 195-201 to synthesize azido-dUMP.

Nucleic acid polymers produced by and utilized with these methods can be single- or double-stranded nucleic acid polymers of any of a wide range of sizes, which may be prepared, purified and/or sequenced as described above.

2. Staudinger Ligation

As already mentioned above some of the methods provided herein generally include a Staudinger ligation reaction. In these methods, the Staudinger ligation occurs between an azide group on a nucleotide analogue incorporated into a nucleic acid polymer and staining agent comprising a substituted triarylphosphine attached to a label.

Optimization of reaction conditions for the Staudinger is within the skill in the art. In certain preferred embodiments, the Staudinger ligation is performed under aqueous conditions. Examples of reaction conditions have been described, for example, in: E. Saxon et al., Science, 2000, 287: 2007-2010; E. Saxon et al., Org. Lett., 2000, 2: 2141-2143; K. L. Kiick et al., Proc. Natl. Acad. Sci. USA, 2002, 99: 19-24: G. A. Lemieux et al., J. Am. Chem. Soc., 2003, 125: 4708-4709; J. A. Prescher et al., Nature, 2004, 430: 873-877.

3. Labels and Detection of Labeled Nucleic Acid Polymers

In some of the methods of the present invention, the Staudinger ligation reaction results in labeling of the nucleic acid polymer.

A. Staining Reagents

In these methods, the label is attached to a substituted triarylphosphine. In certain preferred embodiments, one of the aryl groups of the triarylphosphine is substituted with an electrophilic trap (such as an alkyl ester group). Preferably, the electrophilic trap is located in ortho to the phosphorus atom. The association between the label and the substituted triarylphosphine is preferably covalent. A label can be directly attached to the substituted triarylphosphine or indirectly through a linker.

Methods for attaching detectable moieties to chemical molecules are well-known in the art. In certain embodiments, the label and substituted triarylphosphine are directly, covalently linked to each other. The direct covalent binding can be through an amide, ester, carbon-carbon, disulfide, carbamate, ether, thioether, urea, amine, or carbonate linkage. The covalent binding can be achieved by taking advantage of functional groups present on the substituted triarylphosphine and detectable moieties. Suitable functional groups that can be used to attach the two chemical entities together include, but are not limited to, amines, anhydrides, hydroxy groups, carboxy groups, and thiols. A direct linkage may also be formed using an activating agent, such as a carbodiimide. A wide range of activating agents are know in the art and are suitable for linking a label and a substituted triarylphosphine.

In other embodiments, the label and substituted triarylphosphine are indirectly covalently linked to each other via a linker group. This can be accomplished by using any number of stable bifunctional agents well known in the art, including homofunctional and heterofunctional linkers (see, for example, Pierce Catalog and Handbook), as described above. As described above, the linker may be cleavable to allow temporary labeling of the nucleic acid polymer.

Detectable agents that can be used in the practice of the Staudinger ligation-based methods of the present invention are the same as those that can be used in the practice of the [3+2] cycloaddition methods described above.

The present invention also provides for two- (or more) color labeling of nucleic acid polymers. For example, according to the invention, two different labels may be incorporated into two different nucleic acid polymers. In some embodiments, such incorporation is achieved via two Staudinger ligations: a first Staudinger ligation takes place between a first azide group on a first nucleotide analogue incorporated into a first nucleic acid polymer and a first staining reagent comprising a first label attached to a first substituted triarylphosphine; and a second Staudinger ligation takes place between a second azide group on a second nucleotide analogue incorporated into a second nucleic acid polymer and a second staining reagent comprising a second label attached to a second substituted triarylphosphine. For example, the first and second nucleic acid polymers may be from two different cells, cell populations, cell samples or tissues). The first and second labels are preferably selected such that they produce distinguishable detectable signals. Examples of suitable fluorescent first and second labels have been described above.

B. Detection of Labeled Nucleic Acid Polymers

Detection of nucleic acid polymers labeled via Staudinger ligation can be performed in the same way and using the same techniques as described above for the detection of nucleic acid polymers labeled via [3+2] cycloaddition.

C. Signal-to-Noise Ratio Improvements

In another aspect, the present invention provides a system for improving the signal-to-noise ratio in the detection of a nucleic acid polymer labeled with a fluorescent moiety using a labeling process disclosed herein. Any molecule of staining reagent that has not been consumed by the Staudinger ligation labeling reaction may contribute to the background (i.e., non-specific) signal. The present invention provides a strategy for reducing or eliminating this background signal by quenching the fluorescent signal of the label on the reagent by reaction with a molecule comprising a quenching moiety. For example, in some embodiments, the reaction between the unconsumed reagent and the molecule comprising the quencher moiety is a Staudinger ligation (e.g., the quencher moiety is attached to an azide group that reacts with the triarylphosphine of the unreacted staining reagent).

Thus, certain inventive methods for improving the signal-to-noise ratio in detection of a fluorescently labeled nucleic acid polymer prepared as described herein, comprise contacting unreacted reagent comprising a fluorescent label attached to a substituted triarylphosphine with a molecule comprising a quenching moiety attached to an azide group, such that a Staudinger ligation occurs between the azide and the substituted triarylphosphine. After reaction, the physical proximity between the fluorescent label and the quenching moiety prevents detection of a fluorescent signal from the fluorescent label. Examples of quenching moieties have been described above.

4. Labeling of Nucleic Acid Polymers in Cells

The present invention also provides methods for labeling nucleic acid polymers in cells using a Staudinger ligation. Such methods comprise: contacting a cell with an effective amount of a nucleoside analogue that comprises an azide such that the nucleoside analogue is incorporated into DNA of the cell; contacting the cell with a staining reagent comprising a label attached to a substituted triarylphosphine, such that a Staudinger ligation occurs between the azide and substituted triarylphosphine.

Unless otherwise stated, staining reagent and Staudinger ligation conditions suitable for used in these methods are analogous to those described above for the methods of labeling nucleic acid polymers. Similarly, cells, cell growth conditions, and conditions for incorporation of a nucleoside analogue by DNA replication that are suitable for the present methods are identical to those described above for the [3+2] cycloaddition-based methods.

Following incorporation of the nucleotide analogue into the DNA of in vitro cells, the step of contacting the cells with a staining reagent comprising a label attached to a substituted triarylphosphine may be performed by any suitable method. In some embodiments, the cells are incubated in the presence of the staining reagent in a suitable incubation medium (e.g., culture medium) at 37° C. and for a time sufficient for the reagent to penetrate into the cell and react with any nucleotide analogue incorporated into the DNA of the cells. Optimization of the concentration of staining reagent, Staudinger ligation reaction time and conditions is within the skill in the art.

5. Labeling of Nucleic Acid Polymers in Tissues or Organisms

The present invention also provides methods for labeling nucleic acid polymers in organisms (i.e., living biological systems) using a Staudinger ligation reaction. Such methods comprise: administering to an organism an effective amount of a nucleoside analogue that comprises an azide such that the nucleoside analogue is incorporated into the DNA in cells of the organism; contacting at least one cell of the organism with a staining reagent comprising a label attached to a substituted triarylphosphine such that a Staudinger ligation occurs between the azide and substituted triarylphosphine.

Unless otherwise stated, the staining reagents and Staudinger ligation conditions used in these methods are analogous to those described above for the methods of labeling nucleic acid polymers in cells. Similarly, organisms and conditions for incorporation of nucleoside analogue by DNA replication in living systems that are suitable for the present methods are identical to those described above for the [3+2] cycloaddition-based methods.

Following incorporation of the nucleotide analogue into the DNA of cells of the organisms, the step of contacting at least one cell of the organism with a staining comprising a label attached to a substituted triarylphosphine may be performed by any suitable method that allows for the Staudinger ligation to take place.

6. Isolated Labeled Nucleic Acid Polymers

In another aspect, the present invention provides isolated detectable nucleic acid polymers, for example, prepared by one of the methods described herein, More specifically, the present invention provides nucleic acid polymers that are detectable following a Staudinger ligation reaction as well as isolated nucleic acid polymer that contain at least one detectable moiety that has been incorporated via a Staudinger ligation.

In certain embodiments, an inventive nucleic acid polymer contains at least one nucleotide comprising an azide group. In other embodiments, an inventive nucleic acid polymer contains at least one nucleotide analogue attached to a label. Preferably, the label has been attached through a Staudinger ligation, and contains a amide group and a phosphine oxide function.

The detectable nucleic acid polymer of the present invention may be prepared by any suitable method, as described herein, including synthetic methods and enzymatic methods (e.g., by reverse transcription of total RNA). Such labeled nucleic acid polymers may be used in a wide variety of applications, as described above.

7. Cells Comprising Detectable Nucleic Acid Polymers

In another aspect, the present invention provides cells comprising detectable nucleic acid polymers, for example prepared by one or more of the methods described herein. More specifically, the present invention provides cells comprising nucleic acid polymers that are detectable following a Staudinger ligation as well as cells comprising nucleic acid polymers that contain at least one detectable moiety that has been incorporated via a Staudinger ligation.

III. Determination of DNA Replication/Cellular Proliferation

In another aspect, the present invention provides methods for measuring cell proliferation and/or cell proliferation rates in a cell or an organism.

Such methods may comprise steps of: contacting a cell with an effective amount of a nucleoside analogue that comprises a first reactive unsaturated group such that the nucleoside analogue is incorporated into DNA of the cell; contacting the cell with a reagent comprising a second reactive unsaturated group attached to a label, such that a [3+2] cycloaddition occurs between the first and second reactive unsaturated groups; and determining an amount of label incorporated into the DNA to measure cellular proliferation. In certain embodiments, the amount of label gives information about the extent of cellular proliferation. In other embodiments, the amount of label gives information about the rate of cellular proliferation.

Other methods may comprise steps of: contacting a cell with an effective amount of a nucleoside analogue that comprises an azide such that the nucleoside analogue is incorporated into DNA of the cell; contacting the cell with a staining reagent comprising a label attached to a substituted triarylphosphine, such that a Staudinger ligation occurs between the azide and substituted triarylphosphine; and determining an amount of label incorporated into the DNA to measure cellular proliferation. In some embodiments, the amount of label gives information about the extent of cellular proliferation in the cell. In some embodiments, the amount of label gives information about the rate of cellular proliferation.

Still other methods comprise steps of: administering to an organism an effective amount of a nucleoside analogue that comprises a first reactive unsaturated group such that the nucleoside analogue is incorporated into DNA of cells of the organism; contacting at least one cell of the organism with a reagent comprising a second reactive unsaturated group attached to a label, such that a [3+2] cycloaddition occurs between the first and second reactive unsaturated groups; and determining an amount of label incorporated into the DNA to measure cellular proliferation in the organism. In certain embodiments, the amount of label gives information about the extent of cellular proliferation in the organism. In other embodiments, the amount of label gives information about the rate of cellular proliferation in the organism.

Yet other methods comprise steps of: administering to an organism an effective amount of a nucleoside analogue that comprises an azide such that the nucleoside analogue is incorporated into DNA of cells of the organism; contacting at least one cell of the organism with a staining reagent comprising a label attached to a substituted triarylphosphine, such that a Staudinger ligation occurs between the azide and substituted triarylphosphine; and determining an amount of label incorporated into the DNA to measure cellular proliferation in the organism. In certain embodiments, the amount of label gives information about the extent of cellular proliferation in the organism. In other embodiments, the amount of label gives information about the rate of cellular proliferation in the organism.

These methods may be performed using techniques and procedures as described herein for methods of labeling nucleic acid polymers in cells and organisms. With such methods, the manner of performing the contacting and/or administering steps, type of staining reagent, type of label, and techniques for the detection of such labels are analogous to those described for other methods of the invention relating to labeling nucleic acid polymers in cells or in organisms.

Methods for measuring cellular proliferation or cellular proliferation rates according to the present invention may be used in a wide variety of applications, including, but not limited to characterization of cell lines, optimization of cell culture conditions, characterization of cellular proliferation in normal, diseased and injured tissues, and diagnosis of a variety of diseases and disorders in which cellular proliferation is involved.

A large number of diseases and disorders are known to be characterized by altered cellular proliferation rates and thus can be monitored by methods of the present invention. Such diseases and disorders include, but are not limited to, malignant tumors of any type (e.g., breast, lung, colon, skin, lymphoma, leukemia, and the like); pre-cancerous conditions (e.g., adenomas, polyps, prostatic hypertrophy, ulcerative colitis, and the like); immune disorders such as AIDS, autoimmune disorders, and primary immunodeficiencies; hematologic conditions such as white blood cell deficiencies (e.g., granulocytopenia), anemias of any type, myeloproliferative disorders, lymphoproliferative disorders and the like; organ failure such as alcoholic and viral hepatitis, diabetic nephropathy, myotrophic conditions, premature gonadal failure and the like; conditions affecting bones and muscles, such as osteoporosis; endocrine conditions such as diabetes, hypothyroidism and hyperthyroidism, polycystic ovaries and the like; infectious diseases, such as tuberculosis, bacterial infections, abscesses and other localized tissue infections, viral infections and the like; and vascular disorders, such as atherogenesis, cardiomyopathies, and the like.

IV. Methods of Use

Methods for labeling nucleic acid polymers and for measuring cellular proliferation or cellular proliferate rates as disclosed herein, can be used in a wide variety of applications, some of which are described below.

1. Screening Assays

In another aspect, the present invention provides methods for the identification of agents that perturb cellular proliferation. These methods may be used for screening agents for their ability to induce (i.e., increase, enhance or otherwise exacerbate) or inhibit (i.e., decrease, slow down or otherwise suppress) cell proliferation.

For example, such methods may comprise steps of: (a) contacting a cell with a test agent; (b) contacting the cell with an effective amount of a nucleoside analogue that comprises a first reactive unsaturated group such that the nucleoside analogue is incorporated into DNA of the cell; (c) contacting the cell with a reagent comprising a second reactive unsaturated group attached to a label, such that a [3+2] cycloaddition occurs between the first and second reactive unsaturated groups; (d) determining an amount of label incorporated into the DNA, wherein the amount of label indicates the extent or rate of cellular proliferation; and (e) identifying the test agent as an agent that perturbs cellular proliferation if the amount of label measured in step (d) is less than or greater than the amount of label measured in a control application in which the cell is not contacted with the test agent.

Other methods may comprise steps of: (a) contacting a cell with a test agent; (b) contacting the cell with an effective amount of a nucleoside analogue that comprises an azide such that the nucleoside analogue is incorporated into DNA of the cell; (c) contacting the cell with a reagent comprising a label attached to a substituted triarylphosphine, such that a Staudinger ligation occurs between the azide and substituted triarylphosphine; (d) determining an amount of label incorporated into the DNA, wherein the amount of label indicates the extent or rate of cellular proliferation; and (e) identifying the test agent as an agent that perturbs cellular proliferation if the amount of label measured in step (d) is less than or greater than the amount of label measured in a control application in which the cell is not contacted with the test agent.

In certain embodiments of these methods, the cell is contacted with the test agent after it is contacted with the nucleoside analogue (i.e., step (b) is performed before step (a)).

The manner of performing the steps of contacting the cell; the staining reagent; the label type; and methods of detecting the labeled nucleic acid polymers are analogous to those described for other methods of the invention relating to measuring cellular proliferation and cellular proliferation rates in cells in vitro.

As will be appreciated by one of ordinary skill in the art, the screening methods of the present invention may also be used to identify compounds or agents that regulate cellular proliferation (i.e., compounds or agents that can decrease, slow down or suppress proliferation of over-proliferative cells or that can increase, enhance or exacerbate proliferation of under-proliferative cells).

A. Cells for Screening Assays

The screening assays of the present invention may be performed using any normal or transformed cells that can be grown in standard tissue culture plastic ware. Cells may be primary cells, secondary cells, or immortalized cells. Preferably, cells to be used in the inventive screening methods are of mammalian (human or animal) origin. Cells may be from any organ or tissue origin and of any cell types, as described above.

Selection of a particular cell type and/or cell line to perform a screening assay according to the present invention will be governed by several factors such as the nature of the agent to be tested and the intended purpose of the assay. For example, a toxicity assay developed for primary drug screening (i.e., first round(s) of screening) may preferably be performed using established cell lines, which are commercially available and usually relatively easy to grow, while a toxicity assay to be used later in the drug development process may preferably be performed using primary or secondary cells, which are often more difficult to obtain, maintain, and/or grow than immortalized cells but which represent better experimental models for in vivo situations.

In certain embodiments, the screening methods are performed using cells contained in a plurality of wells of a multi-well assay plate. Such assay plates are commercially available, for example, from Strategene Corp. (La Jolla, Calif.) and Corning Inc. (Acton, Mass.), and include, for example, 48-well, 96-well, 384-well and 1536-well plates.

B. Test Agents

As will be appreciated by those of ordinary skill in the art, any kind of compounds or agents can be tested using the inventive methods. A test compound may be a synthetic or natural compound; it may be a single molecule, a mixture of different molecules or a complex of different molecules. In certain embodiments, the inventive methods are used for testing one or more compounds. In other embodiments, the inventive methods are used for screening collections or libraries of compounds.

Compounds that can be tested for their capacity or ability to perturb (i.e., induce or inhibit) or regulate cell proliferation can belong to any of a variety of classes of molecules including, but not limited to, small molecules, peptides, saccharides, steroids, antibodies (including fragments or variants thereof), fusion proteins, antisense polynucleotides, ribozymes, small interfering RNAs, peptidomimetics, and the like.

Compounds or agents to be tested according to methods of the present invention may be known or suspected to perturb or regulate cell proliferation. Alternatively, the assays may be performed using compounds or agents whose effects on cell proliferation are unknown.

Examples of compounds that may affect cell proliferation and that can be tested by the methods of the present invention include, but are not limited to, carcinogens; toxic agents; chemical compounds such as solvents; mutagenic agents; pharmaceuticals; particulates, gases and noxious compounds in smoke (including smoke from cigarette, cigar and industrial processes); food additives; biochemical materials; hormones; pesticides; ground-water toxins; and environmental pollutants. Examples of agents that may affect cell proliferation and that can be tested by the methods of the present invention include, but are not limited to, microwave radiation, electromagnetic radiation, radioactive radiation, ionizing radiation, heat, and other hazardous conditions produced by or present in industrial or occupational environments.

C. Identification of Agents that Induce or Inhibit Cellular Proliferation

According to screening methods of the present invention, determination of the ability of a test agent to perturb or regulate cellular proliferation includes comparison of the amount of label incorporated into DNA of a cell that has been contacted with the test agent with the amount of label incorporated into DNA of a cell that has not been contacted with the test agent.

A test agent is identified as an agent that perturbs cellular proliferation if the amount of label incorporated into DNA of the cell that has been contacted with the test agent is less than or greater than the amount of label measured in the control cell. More specifically, if the amount of label incorporated into DNA of the cell that has been contacted with the test agent is less than the amount of label measured in the control cell, the test agent is identified as an agent that inhibits cell proliferation. If the amount of label incorporated into DNA of the cell that has been contacted with the test agent is greater than the amount of label measured in the control cell, the test agent is identified as an agent that induces cell proliferation.

Reproducibility of the results may be tested by performing the analysis more than once with the same concentration of the test agent (for example, by incubating cells in more than one well of an assay plate). Additionally, since a test agent may be effective at varying concentrations depending on the nature of the agent and the nature of it mechanism(s) of action, varying concentrations of the test agent may be tested (for example, added to different wells containing cells). Generally, test agent concentrations from 1 fM to about 10 mM are used for screening. Preferred screening concentrations are between about 10 pM and about 100 µM.

In certain embodiments, the methods of the invention further involve the use of one or more negative or positive control compounds. A positive control compound may be any molecule or agent that is known to perturb (i.e., induce or inhibit) or regulate cellular proliferation. A negative control compound may be any molecule or agent that is known to have no detectable effects on cellular proliferation. In these embodiments, the inventive methods further comprise comparing the effects of the test agent to the effects (or absence thereof) of the positive or negative control compound.

As will be appreciated by those skilled in the art, it is generally desirable to further characterize an agent identified by the inventive screening methods as an agent that perturbs or an agent that regulates cellular proliferation. For example, if a test compound has been identified as an agent that perturbs (or regulates) cellular proliferation using a given cell culture system (e.g., an established cell line), it may be desirable to test this ability in a different cell culture system (e.g., primary or secondary cells).

Test agents identified by the screening methods of the invention may also be further tested in assays that allow for the determination of the agents' properties in vivo.

Accordingly, the present invention provides methods for identifying an agent that perturbs cellular proliferation or cell proliferation rate in vivo. Such methods comprise steps of: (a) exposing an organism to a test agent; (b) administering to the organism an effective amount of a nucleoside analogue that comprises a first reactive unsaturated group such that the nucleoside analogue is incorporated into DNA of cells of the organism; (c) contacting at least one cell of the organism with a reagent comprising a second reactive unsaturated group attached to a label, such that a [3+2] cycloaddition occurs between the first and second reactive unsaturated group; (d) determining an amount of label incorporated into the DNA, wherein the amount of label indicates the extent of cellular proliferation or rate of cellular proliferation; and (e) identifying the test agent as an agent that perturbs cellular proliferation in the organism if the amount of label measured in step (d) is less than or greater than the amount of label measured in a control application in which the organism is not exposed to the test agent.

The present invention also provides methods for identifying an agent that perturbs cellular proliferation or cell proliferation rate in vivo. Such methods comprise steps of: (a) exposing an organism to a test agent; (b) administering to the organism an effective amount of a nucleoside analogue that comprises an azide such that the nucleoside analogue is incorporated into DNA of cells of the organism; (c) contacting at least one cell of the organism with a staining reagent comprising a label attached to a substituted triarylphosphine, such that a Staudinger ligation occurs between the azide and substituted triarylphosphine; (d) determining an amount of label incorporated into the DNA, wherein the amount of label indicates the extent of cellular proliferation or rate of cellular proliferation; and (e) identifying the test agent as an agent that perturbs cellular proliferation in the organism if the amount of label measured in step (d) is less than or greater than the amount of label measured in a control application in which the organism is not exposed to the test agent.

In certain embodiments, the test agent is administered after the organism has been contacted with the nucleoside analogue (i.e., step (b) is performed prior to step (a)).

As will be appreciated by one of ordinary skill in the art, these methods can be used to identify agents that regulate cellular proliferation in vivo.

The manner of administration, staining reagent, type of label and method of detection of the labeled nucleic acid polymers are analogous to those described herein for other methods of the invention relating to measuring cellular proliferation in living systems.

2. Cell Cycle Studies

The labeling methods of the present invention, which do not require fixation and denaturation and are therefore suitable for application in living cells, can be used in studies of the complex spatio-temporal mechanisms of the cell cycle. A clear understanding of the mechanism of cell cycle in the presence or absence of various perturbations can pave the way to the development of new therapeutic approaches for controlling or treating human diseases, such as cancer. Until recently, most studies of nuclear architecture were carried out in fixed cells (A. I. Lamond and W. C. Earnshaw, Science, 1998, 280: 457-553). However, time-lapse fluorescence microscopy imaging has since been demonstrated to allow live cell nuclei to be observed and studied in a dynamic fashion, and to provide far richer information content than conventional fixed cell microscopy techniques (Y. Hiraoka and T. Haraguchi, Chromosome Res., 1996, 4: 173-176; T. Kanda et al., Curr. Biol., 1998, 8: 377-385).

Figure 11:
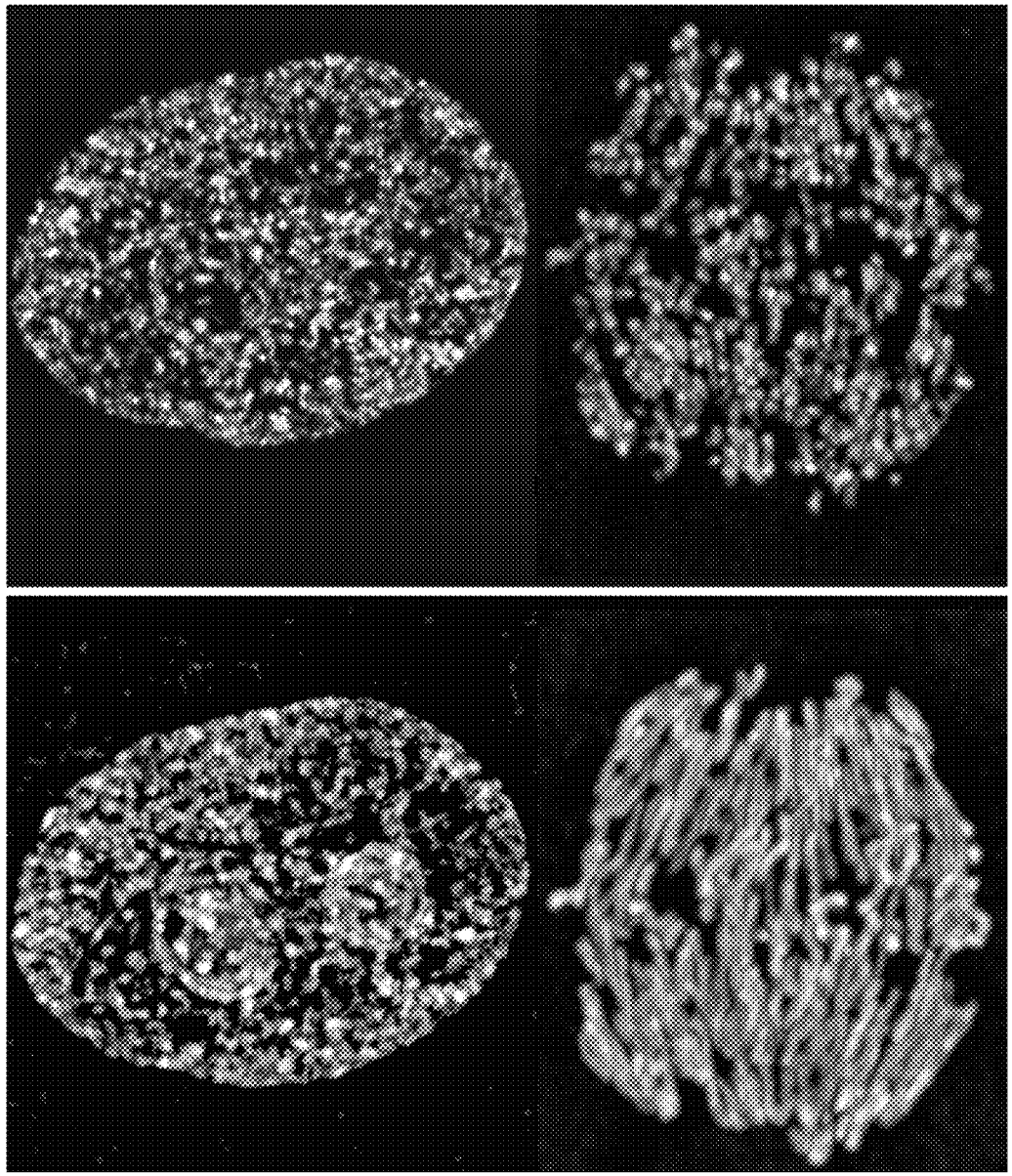
FIG. 11 presents two sets of high resolution images of two cells labeled with EdU. Images (A) and (B) on the left show EdU-labeled cells stained with OliGreen, a dye that stains total cellular DNA. Images (C) and (D) on the right show EdU-labeled cells stained with Xrhodamine-azide. The top images show the cell in interphase, while the images at the bottom show the cells in anaphase.

As shown on FIG. 11, the methods of the present invention allow specific labeling of DNA undergoing replication as well as characterization of a cell as mitotic (e.g., anaphase) or interphase. Thus, combining the labeling methods disclosed herein and imaging techniques such as time-lapse fluorescence microscopy or flow cytometry can help acquire fundamental knowledge about the cell cycle of different cell types under various perturbation conditions and allow the development of new drugs that affect the cell cycle.

Thus, the methods of the present invention may be applied to the study of a large variety of pathological conditions. For example, cancer is increasingly viewed as a cell cycle disease. This view reflects the evidence that the vast majority of tumors have suffered defects that derail the cell cycle machinery leading to increased cell proliferation. Such defects can target either components of the cell cycle itself or elements of upstream signaling cascades that eventually converge to trigger cell cycle events. Cancer is not the only clinical condition thought to be associated with cell cycle deregulation (M. D. Garrett, Curr. Sci. 2001, 81: 515-522). For example, the mechanism by which neurons die in human neurodegenerative diseases remains an enigma till today (I. Vincent et al., Prog. Cell Cycle Res., 2003, 5: 31-41). Terminally differentiated neurons of normal brains are incapable of cell division. However, accumulating evidence has suggested that aberrant activation of the cell cycle in certain neurodegenerative diseases leads to their demise. Elucidating the details of this cell cycle-mediated degenerative cascade may lead to novel strategies for curbing the onset and progression of certain neurodegenerative diseases. Similarly, it is known that manipulation of cell division can have beneficial or pathological consequences on cardiovascular function (M. Boehm and E. G. Nabel, Prog. Cell Cycle Res., 2003, 5: 19-30). The inability of cardiomyocytes to proliferate and regenerate following injury results in an impairment of cardiac function associated with physical impediment and may lead to death. The genetic program in the cardiomyocytes that leads to their inability to proliferate and regenerate is not understood, but if identified, it could lead to therapies aimed at re-initiating the cell cycle and proliferation in cardiomyotes.

3. Chromosomal Structures

The labeling methods of the present invention can also be used for the study of chromosomes' ultrastructures.

Figure 12:
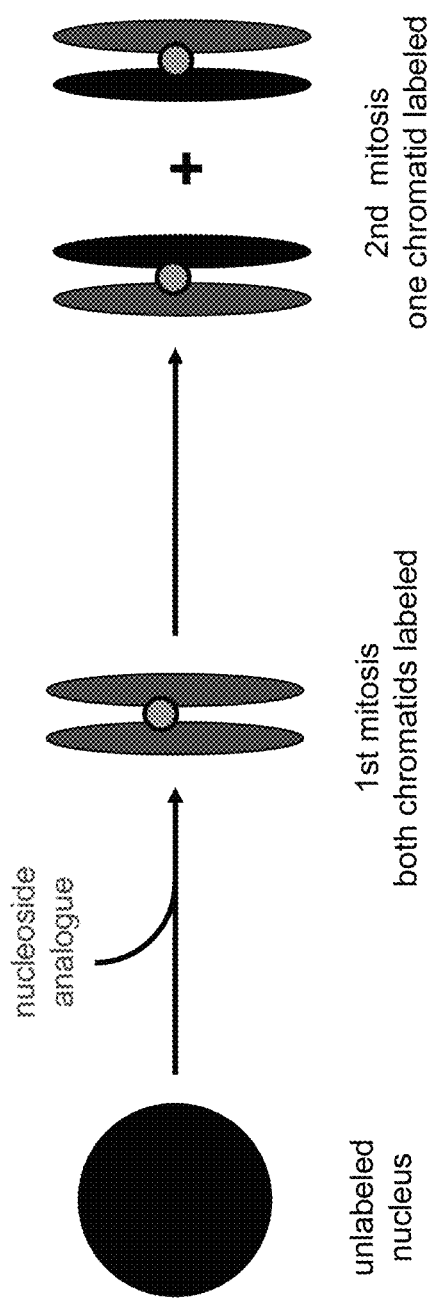
FIG. 12 is a scheme showing the procedure followed to label only one DNA molecule of the two that form a chromosome.

For example, the labeling methods of the present invention may be used to study sister chromatic exchange (SCE). SCE is a natural process in which two sister chromatids break and rejoin with one another physically switching positions on the chromosome (S. Wolf, Annu. Rev. Genet., 1977, 11: 183-201; S. A. Latt, Annu. Rev. Genet., 1981, 15: 11-53). Such exchanges take place during cell replication with about 10 SCEs occurring spontaneously in normally cycling human cells (P. E Crossen et al., Hum. Genet., 1977, 35: 345-352; S. M. Galloway and H. J. Evans, 1975, 15: 17-29). SCEs can also be induced by various genotoxic treatments (L. Hagmar et al., Cancer Res., 1998, 58: 4117-4121) suggesting that SCEs reflect a DNA repair process. Detection of SCEs requires some means of differentially labeling sister chromatids and that has traditionally been done by growing cells in a medium containing BrdU for the duration of two complete cell cycles. The labeling methods of the present invention may be used instead of BrdU (see FIG. 12). As shown on FIG. 13, the labeling methods disclosed herein allow staining of only one DNA molecule of the two that form a chromosome.

The labeling methods of the present invention may also be used as a new tool to study kinetochore-microtubule interactions and centromeric cohesion. Proper segregation of chromosomes during cell division is essential for the maintenance of genetic stability. During this process chromosomes must establish stable functional interactions with microtubules through the kinetochore, a specialized protein structure located on the surface of the centromeric heterochromatin. Stable attachment of kinetochores to a number of microtubules results in the formation of a kinetochore fiber that mediates chromosome movement. Although the fidelity of chromosome segregation depends on precise interactions between kinetochores and microtubules, it is still unclear how this interaction is mediated and regulated (M. B. Gordon et al., J. Cell Biol., 2001, 152: 425-434; A. A. Van Hooser and R. Heald, Curr. Biol., 2001, 11: R855-857; S. Biggins and C. E. Walczak, Curr. Biol., 2003, 13: R449-460; H. Maiato et al., J. Cell Sci., 2004, 117: 5461-5477; H. Maiato and C. E. Sunkel, Chromosome Res., 2004, 12: 585-597) The centromere is a specialized region of the chromosome that is essential for proper segregation of the chromosomes during cell division. It is the site at which the kinetochore is assembled. During mitosis, replicated sister chromatids must maintain cohesion as they attach to the mitotic spindle. At anaphase, cohesion is lost simultaneously along the entire chromosome, releasing sisters from one another and allowing them to segregate to opposite poles. The molecular mechanism(s) responsible for chromatic cohesion during mitosis remain(s) ambiguous (K. J. Dej and T. L. Orr-Weaver. Trends Cell Biol., 2000, 10: 392-399; T. Fukagawa, Chromosome Res., 2004, 12: 557-567; S. Salic et al., Cell, 2004, 118: 567-578).

4. Labeling of RNA and RNA Localization Studies

The labeling methods of the present invention may be used for labeling RNA.

Certain inventive methods include a [3+2] cycloaddition between a first reactive unsaturated group on a nucleotide analogue incorporated into a ribonucleotide polymer and a second reactive unsaturated group attached to a label. The [3+2] cycloaddition reaction results in labeling of the ribonucleotide polymer.

Other methods of the present invention include a Staudinger ligation between an azide group on a nucleotide analogue incorporated into a ribonucleotide polymer and a substituted triarylphosphine attached to a label. The Staudinger ligation results in labeling of the ribonucleotide polymer.

In such methods, the ribonucleotide polymer comprising the nucleotide analogue may be prepared by any suitable method, as known in the art. For example, the ribonucleotide polymer may be synthesized by in vitro transcription of DNA, cloned downstream of T3, T7 or SP6 polymerases promoters in the presence of nucleotide triphosphates (including the nucleotide analogue triphosphate) as substrates. Alternatively, the ribonucleotide polymer may be prepared using amplification methods.

The inventive labeling methods may be used in microarray hybridization assays to measure mRNA transcript levels of many genes in parallel.

The inventive labeling methods may also find applications in ribosome display, a cell-free system for the in vitro selection of proteins and peptides (C. Tuerk and L. Gold, Science 1990, 249: 505-510; G. F. Joyce, Gene 1989, 82: 83-87; J. W. Szostak, Trends Biochem. Sci. 1992, 17: 89-93; D. E. Tsai et al., Proc. Natl. Acad. Sci. USA, 1992, 89: 8864-8868; J. A. Doudna et al., Proc. Natl. Acad. Sci. USA, 1995, 92: 2355-2359; C. Shaffitzel et al., J. Immunol. Methods, 1999, 231: 119-135; D. Lipovsel and A. Pluckthun, J. Immunol. Methods, 2001, 290: 51-67; A. M. Jackson et al., Brief Funct. Genomic Protreomic, 2004, 2: 308-319). These selection assays generally involve adding an RNA library to the protein or molecule of interest, washing to remove unbound RNA, and specifically eluting the RNA bound to the protein. The RNA is then reversed-transcribed and amplified by PCR. The cDNA obtained is then transcribed in the presence of nucleotide analogues for detection purposes. Those molecules that are found to bind the protein or other molecule of interest are cloned and sequenced to look for common sequences. The common sequence is then used to develop therapeutic oligonucleotides.

The RNA labeling methods of the present invention may also be used for visualizing mRNA movement (transport and localization) in living cells. mRNA localization is a common mode of post-transcriptional regulation of gene expression that targets a protein to its site of function (I. M. Palacios and D. St Johnston, Annu. Rev. Cell Dev. Biol., 2001, 17: 569-614; R. P. Jansen, Nature Rev. Mol. Cell Biol., 2001, 2: 247-256; M. Kloc et al., Cell, 2002, 108: 533-544). Many of the best characterized localized mRNAs are found in oocytes and early embryos, where they function as localized determinants that control axis formation and the development of the germline. mRNA localization has also been shown to play an important role in somatic cells, such as neurons, where it may be involved in learning and memory. Different mRNA visualization methods have been developed to identify the machinery and mechanisms involved in mRNA transport and localization, including aminoally-uridine triphosphate incorporation into RNA followed by fluorescein or rhodamine coupling and direct incorporation of Alexa-Fluor-uridine triphosphate into RNA. (V. Van de Bor and I. Davis, Curr. Opin. Cell Biol., 2004, 16: 300-307). mRNA molecules fluorescently labeled in vitro according to the present invention may be introduced into living cells and their movement monitored in real time.

V. Kits

In another aspect, the present invention provides kits comprising materials useful for carrying out one or more of the methods of the invention. The inventive kits may be used by diagnostic laboratories, clinical laboratories, experimental laboratories, or practitioners. The invention provides kits which can be used in these different settings.

Basic materials and reagents for labeling nucleic acid polymers according to the present invention may be assembled together in a kit. An inventive kit for labeling a nucleic acid polymer may include at least one nucleoside analogue that comprises a first reactive unsaturated group; and a reagent comprising a second reactive unsaturated group attached to a label. An inventive kit for dual labeling of a nucleic acid polymer may include at least one first nucleoside analogue that comprises a first reactive unsaturated group; at least one second nucleoside analogue that comprises a second reactive unsaturated group; a first reagent comprising a third reactive unsaturated group attached to a first label; and a second reagent comprising a fourth reactive unsaturated group attached to a second label. Alternatively or additionally, an inventive kit for labeling a nucleic acid polymer may include at least one nucleoside analogue that comprises an azide group; and a reagent comprising a label attached to a substituted triarylphosphine. An inventive kit for differential labeling of two nucleic acid polymers may comprise at least one first nucleoside analogue comprising an azide group; at least one second nucleoside analogue comprising an azide group; a first staining reagent comprising a first label attached to a substituted triarylphosphine and a second staining reagent comprising a second label attached to a substituted triarylphosphine.

Each kit preferably comprises the reagents which render the procedure specific. Thus, if the detectable agent is a hapten, the kit will preferably comprise the corresponding appropriate antibody. Similarly, a kit intended to be used for the labeling of nucleic acid polymers in living organisms will contain nucleosides formulated such that they can be administered to a living organism. A kit intended to be used for screening compounds for their ability to induce or inhibit cellular proliferation may include cells comprising labeled nucleic acid polymers of the present invention.

Certain inventive kits may further comprise buffers and/or reagents useful to perform a [3+2] cycloaddition reaction, such as aqueous medium and Cu(I). Other inventive kits may further comprise buffers and/or reagents useful to perform a Staudinger ligation reaction.

An inventive kit may further comprise one or more of: wash buffers and/or reagents, cell fixation buffers and/or reagents, immunohistochemical buffers and/or reagents, DAB photoconversion buffers and/or reagents, and detection means. The buffers and/or reagents are preferably optimized for the particular labeling/detection technique for which the kit is intended. Protocols for using these buffers and reagents for performing different steps of the procedure may also be included in the kit.

Kits may also contain instruments (e.g., needle biopsy syringe) and/or reagents for the isolation of cells from an organism.

The reagents may be supplied in a solid (e.g., lyophilized) or liquid form. The kits of the present invention optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the labeling/detection assay may also be provided. The individual containers of the kit are preferably maintained in close confinement for commercial use.

Instructions for using the kit according to one or more methods of the invention may comprise instructions for labeling nucleic acid polymers, instructions for measuring cellular proliferation, instructions for interpreting the results obtained as well as a notice in the form prescribed by a governmental agency (e.g., FDA) regulating the manufacture, use or sale of pharmaceuticals or biological products.

EXAMPLES

The following examples describe some of the preferred modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Example 1: General Protocols for Labeling of Cells with Ethynyl-dU

Ethynyl-dU (EdU) was used in tissue culture media (DMEM complemented with penicillin, streptomycin, and fetal calf serum (FCS)) ranging from 10 nM to 1 μM depending on the length of the labeling pulse. For example, if cells to be labeled were synchronized in the S phase, 100 nM to 1 μM of EdU was used for 1 to 2 hours. After labeling, the cells were washed 3 or 4 times with PBS and then tissue culture media was added.

Staining of Living Cells:

Staining Solution: 100 mM Tris pH 8.5 (from 2 M stock in water), 0.5 to 1 mM $CuSO_4$ (from 1 M stock in water), 0.5 to 1 μM TMR-propyl-azide (from approximately 100 mM stock in DMF), and water (as required) were mixed together. Ascorbic acid (from a 0.5 mM stock in water) was then added to this solution to a final concentration of 50 mM, and the resulting staining solution is mixed thoroughly.

For staining cells alive without permeabilization (e.g., when the staining reagent was TMR-propyl-azide, which is cell permeable), tissue culture media was removed and replaced by the staining solution described above. Cells were incubated for at least 30 minutes in the presence of the staining solution although staining is generally complete after 10 minutes of incubation. After staining, unreacted TMR-propyl-azide was removed by washing with buffer (such as PBS or TBS) containing 0.5% Triton-X100 (or similar detergent). Washes with methanol or ethanol may be performed to obtain low background If desired, cell fixation can be performed at the same time by adding 3% formaldehyde (or glutaraldehyde) to the washing buffer. In this case, cells were incubated in the washing buffer for at least 10 minutes at room temperature.

Staining of Fixed Cells:

Staining Solution: 100 mM Tris pH 8.5 (from 2 M stock in water), 0.5 to 1 mM $CuSO_4$ (from 1 M stock in water), 0.5 to 1 μM fluorophore-azide (from approximately 10-100 mM stock in DMSO), and water (as required) were mixed together. Ascorbic acid (from a 0.5 mM stock in water) was then added to this solution to a final concentration of 50-100 mM, and the resulting staining solution is mixed thoroughly using a vortex.

Cells can be fixed by any suitable method, e.g., cells can be fixed by aldehyde fixation (formaldehyde or glutaraldehyde), with or without permeabilization. After fixation, the cells were washed in buffer with or without non-ionic detergent (0.2-0.5% Triton X100). Before staining, cells were rinsed with buffer without detergent (PBS or TBS). The cells were then incubated in the presence of the staining solution for at least 30 minutes. Overnight staining is preferably performed in a cold room.

Following staining, the cells were washed several times with a buffer containing 0.5% of detergent. Washes with methanol or ethanol can be performed to significantly reduce the background if necessary.

Stained Cells Imaging:

Stained cells can then be immunostained using standard protocols. Cells were then mounted in standard mounting media and imaged. Whether mounted or not, the stain was found to be very stable indefinitely at 4° C.

Example 2: Labeling of HeLa Cells with Ethynyl-dU

HeLa cells were labeled or not with 1 μM EdU as described in Example 1. They were then fixed/permeabilized and stained with an Xrhodamine-azide reagent (which is not cell permeable and therefore requires permeabilization in order to perform the click chemistry).

Figure 5:
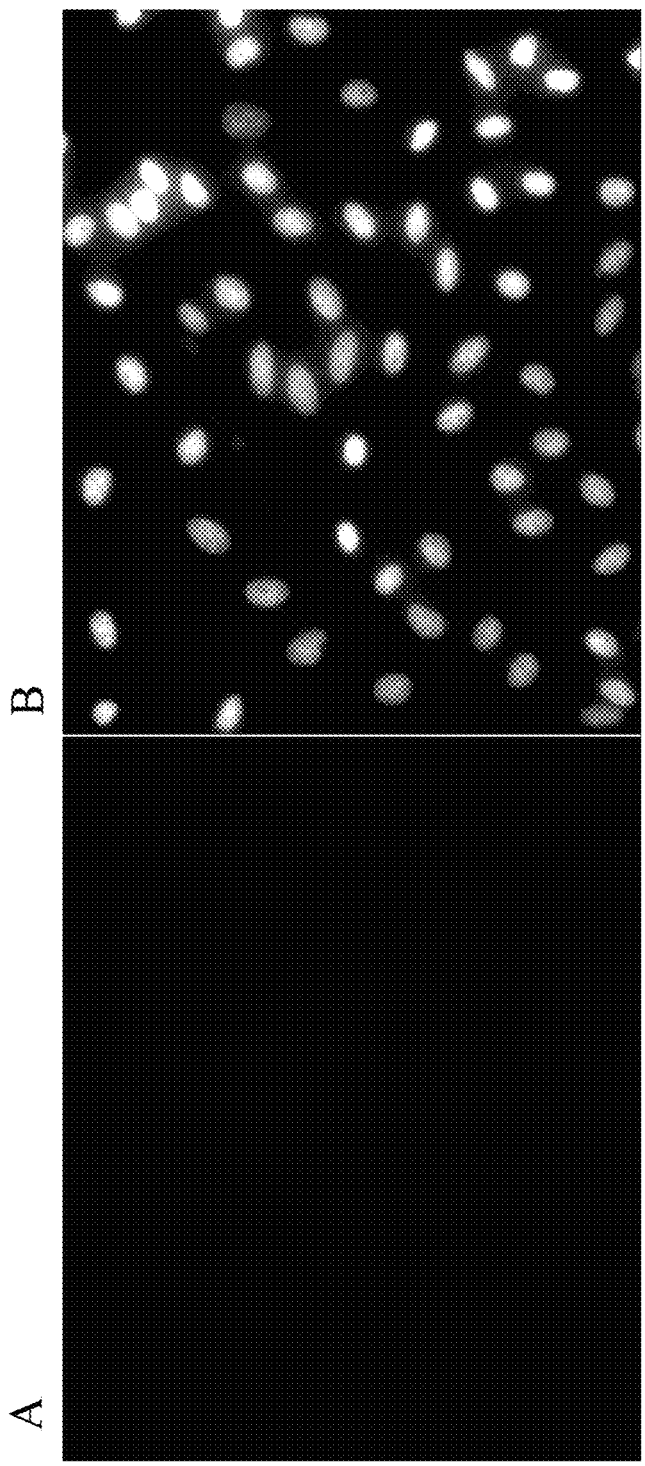
FIG. 5 presents two images obtained by fluorescence microscopy of (A) EdU-unlabeled HeLa cells stained with XRhodamine-azide and (B) EdU-labeled cells stained with XRhodamine-azide as described in Example 2.

Images of both populations of cells (i.e., labeled or not with EdU) are presented on FIG. 5. A higher resolution view of these cells is presented in FIG. 11 (right), along with images obtained from EdU-labeled HeLa cells stained with OliGreen (FIG. 11 left). Note the speckled appearance of the EdU stain in the bottom cell which is undergoing anaphase. The speckles are due to the fact that the labeling pulse of EdU was shorter than the time required for the cell to replicate its DNA; thus only the DNA replicating during the pulse was labeled.

Example 3: Time-Lapse Fluorescence Imaging of Labeled Live Cells

To stain DNA under conditions as close to the native state as possible, a cell-permeable TMR-azide reagent was developed. TMR-propyl-azide was synthesized by first reacting TMR-carboxy-NHS ester with 3-bromo-propylamine to form bromo-propyl-TMR. The latter compound was then reacted with sodium azide to form TMR-propyl-azide, which was found to be cell-permeable and thus suitable for labeling cells without the need for permeabilization and/or fixation.

To demonstrate staining of cells using TMR-propyl-azide, HeLa cells were first labeled with EdU. To facilitate live microscopic imaging, EdU-labeled cells were plated in coverslip chambers which were mounted on the heated stage (37° C.) of an inverted Nikon TE200)U microscope equipped for wide-field fluorescence microscopy as well as spinning-disk confocal fluorescence microscopy (Yokogama spinning disk confocal head from Perkin-Elmer). The media covering the cells was removed and replaced with a staining solution containing 200 nM TMR-propyl-azide, 25 mM ascorbate and 1 mM copper (II) sulfate dissolved in physiological saline buffer. The cells were imaged by time-lapse fluorescent microscopy (one frame every 15 seconds) to detect the TMR signal accumulating in the nuclei of the EdU-labeled cells.

Figure 6:
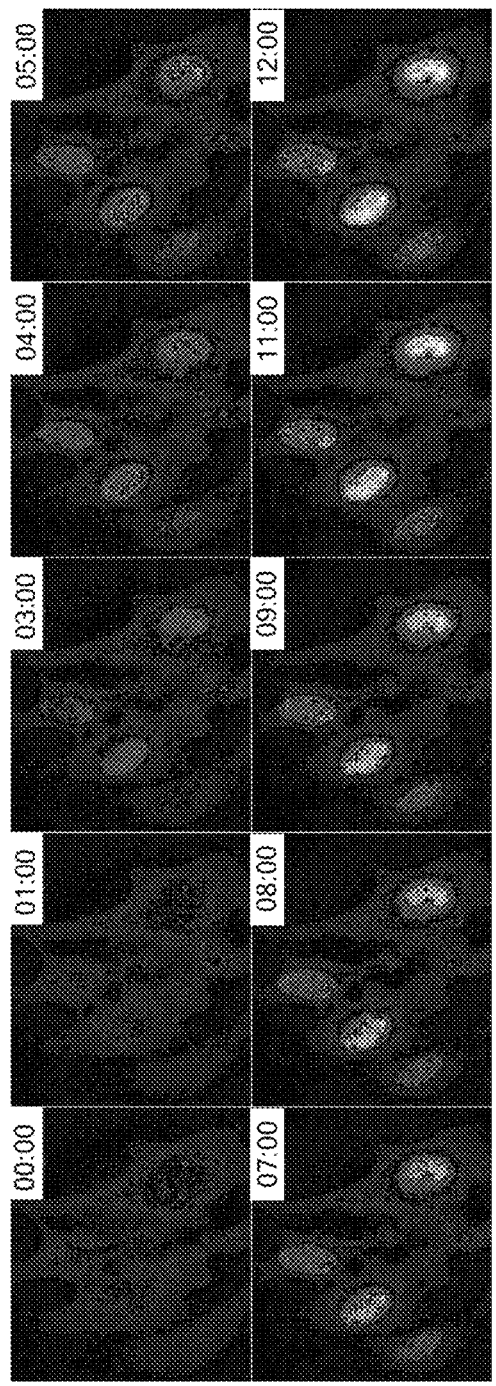
FIG. 6 presents of set of time-lapse fluorescence microscopy images showing the staining reaction on live cells as a function of time. Staining of EdU-labeled cells was performed using a cell-permeable TMR-azide, as described in Example 3. Indications of time on the images are given in minutes:seconds.
Figure 7:
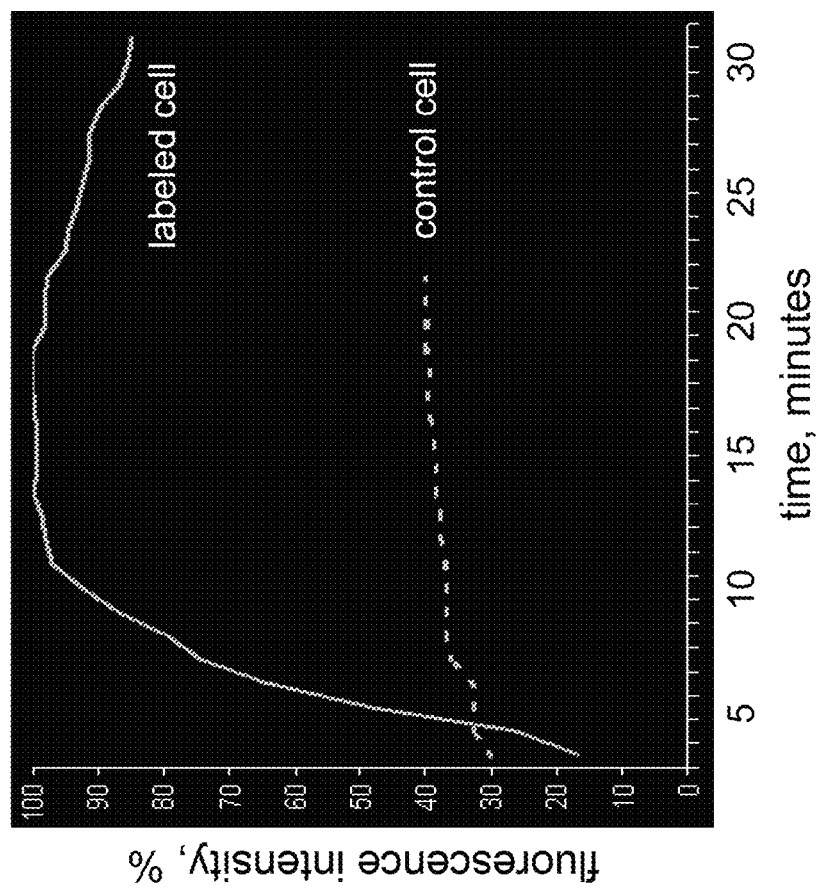
FIG. 7 is a graph showing the DNA staining intensity plotted over time as measured on the images presented on FIG. 6.

A shown on FIG. 6 (which presents images obtained by time-lapse fluorescence microscopy), the click reaction was found to work very well on live cells using this cell permeable reagent. As shown on FIG. 7, EdU detection was complete within minutes.

Example 4: In Vivo Labeling

BLAB/C mice were injected with 200 micrograms of EdU intraperitoneally. Three days later, organs were harvested, fixed, embedded in paraffin and sectioned. The sections were then de-waxed and stained with Xrhadomine-azide for 5 minutes, stained with Hoechst, washed and then mounted.

Figure 8:
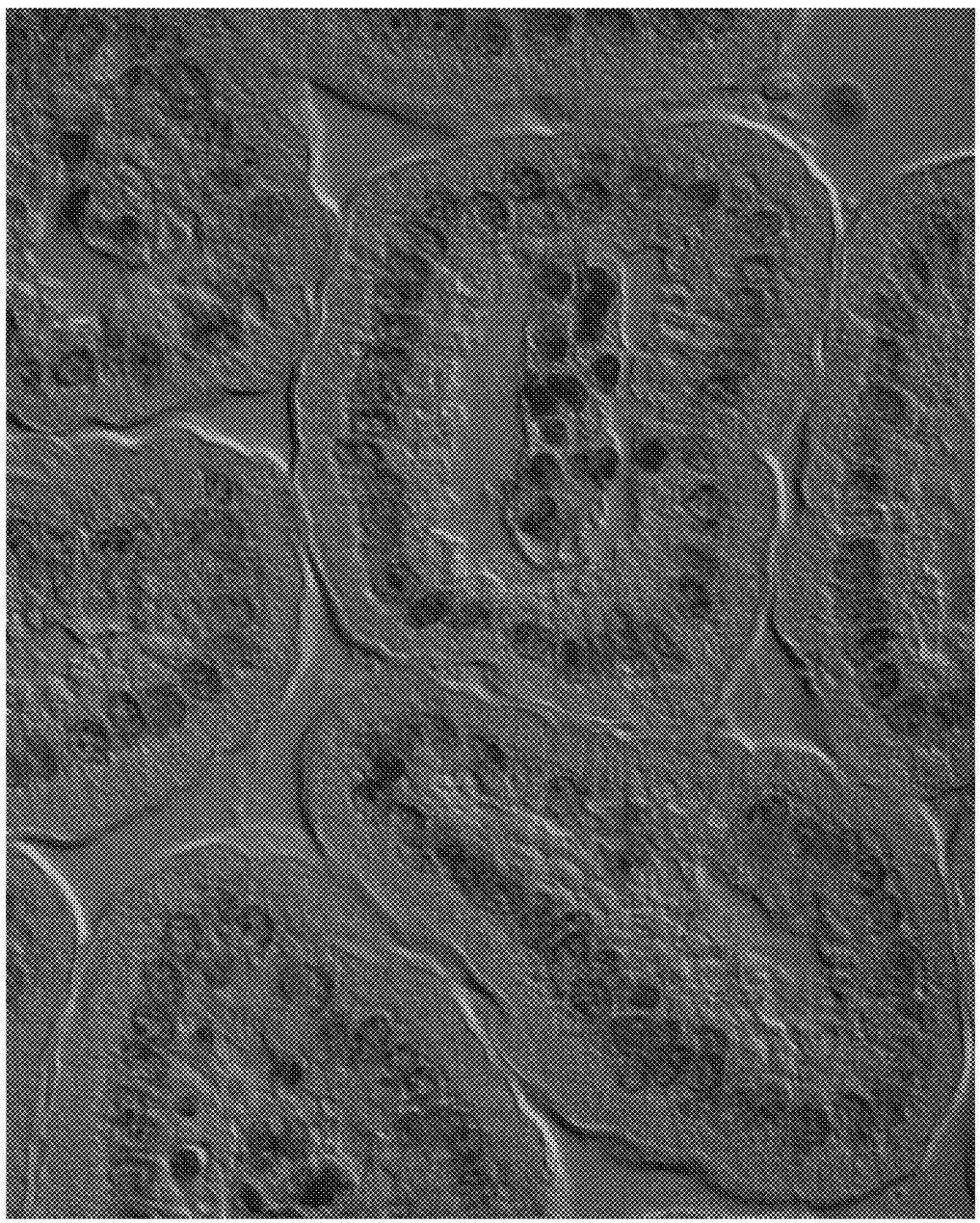
FIG. 8 shows a fluorescence microscopy image (high magnification) of a section through a mouse intestine labeled as described in Example 4. The cells with red nuclei are the cells which incorporated EdU and their descendants. DNA appears in blue (Hoechst).
Figure 9:
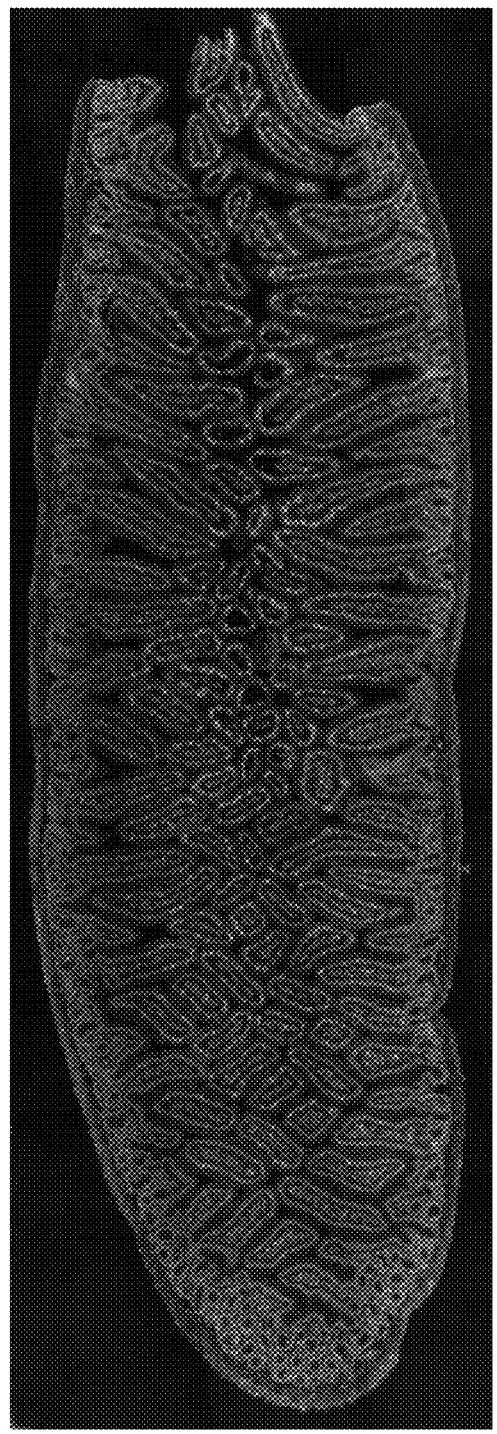
FIG. 9 shows a fluorescence microscopy image (low magnification) of a section through a mouse intestine labeled as described in Example 4. DNA appears in green. Red indicates the cells which incorporated EdU and their descendants. The object presented on this figure is an entire oblique section through the intestine—about half a centimeter in length.

FIG. 8 shows a high magnification (400×) of a section through the intestine. The cells with red nuclei are the cells which incorporated EdU and their descendants. DNA appears in blue. FIG. 9 is a composite of image of many 400× images stitched together to form the image of a large piece of a mouse intestine section (DNA appears in green). The object is an entire oblique section through the intestine—about half a centimeter in length.

Figure 10:
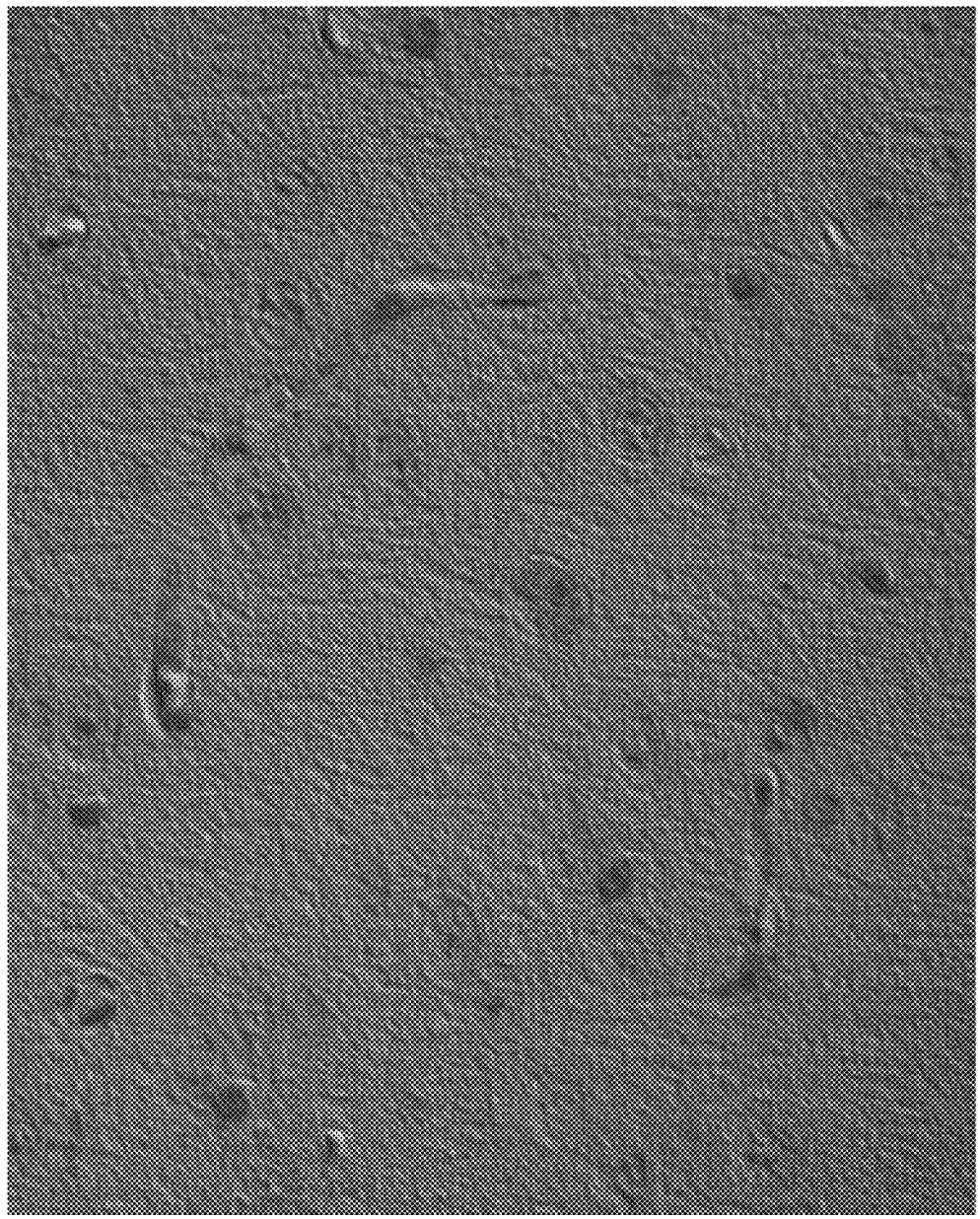
FIG. 10 shows a fluorescence microscopy image of a section through a mouse brain labeled as described in Example 4. As sole EdU-labeled cell can be easily identified on this brain section (cells of the brain almost never divide, unlike cells of the intestine, which are highly proliferative).

FIG. 10 is a section through the mouse brain, an organ whose cells almost never divide (unlike the intestine, which is highly proliferative). A sole EdU-labeled cell can be easily identified on this brain section.

Example 5: Tracing a Single Sister Chromatic at the Centromere

The purpose of the experiment reported herein was to label only one DNA molecule of the two that form a chromosome. That was accomplished by pulsing HeLa cells with EdU during DNA synthesis followed by a chase lasting two cell cycles, as depicted on FIG. 12.

Figure 13:
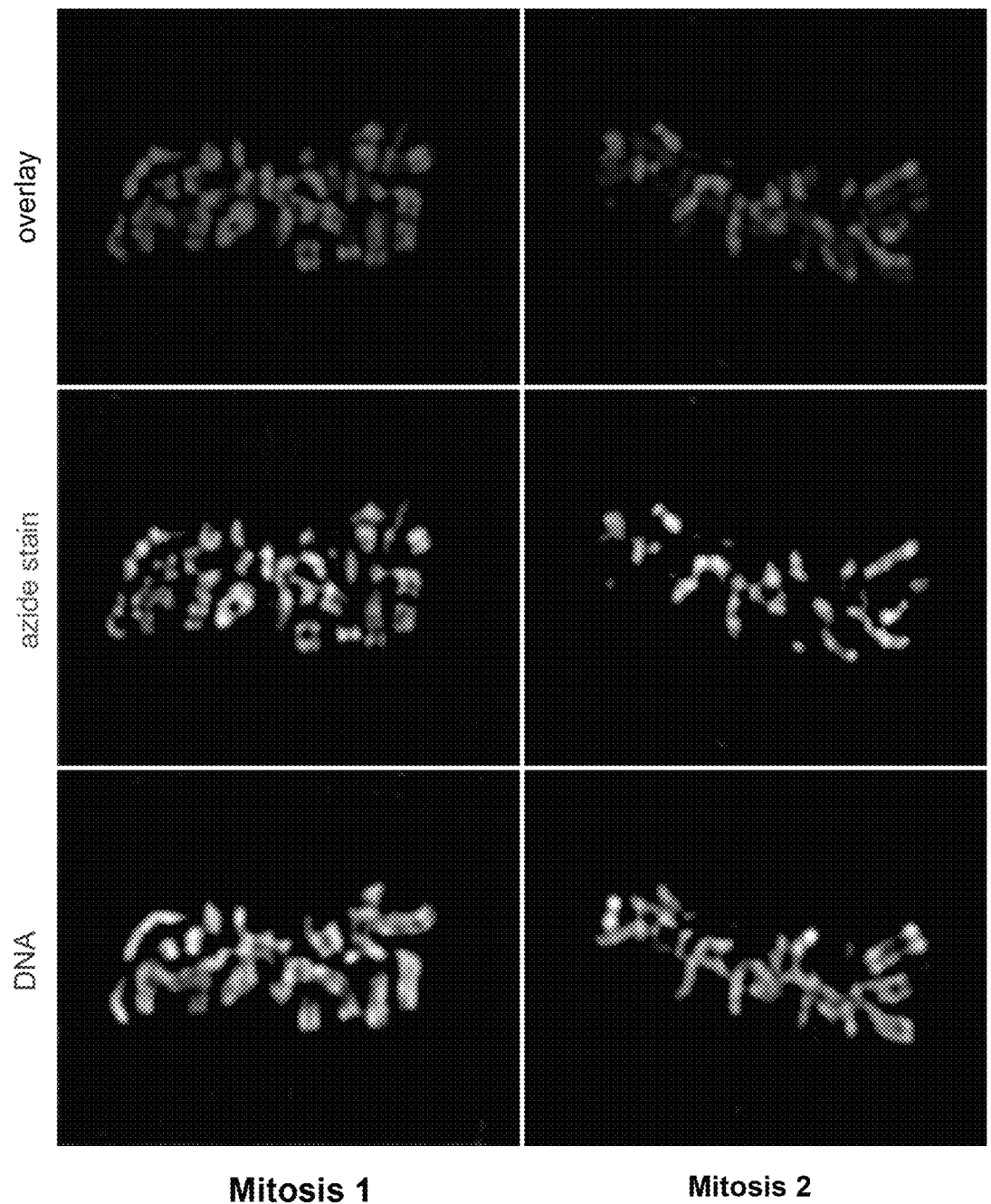
FIG. 13 is a set of images of the DNA of a EdU-labeled cell stained with Alexa 568-azide as described in Example 5. The first row of images show the DNA, azide stain and an overlay of the two after the first mitosis. The second row of images show the DNA, azide stain and an overlay of the two after the second mitosis.

In the first mitosis after labeling, both DNA molecules were labeled while in the second mitosis only one DNA molecule was labeled. EdU allowed very nice resolution imaging of chromosomes in cells as shown by FIG. 13. In these experiments, Alexa568-azide was used for the staining and the staining process involved permeabilization.

Example 6: Labeling of RNA in Cells

Figure 14:
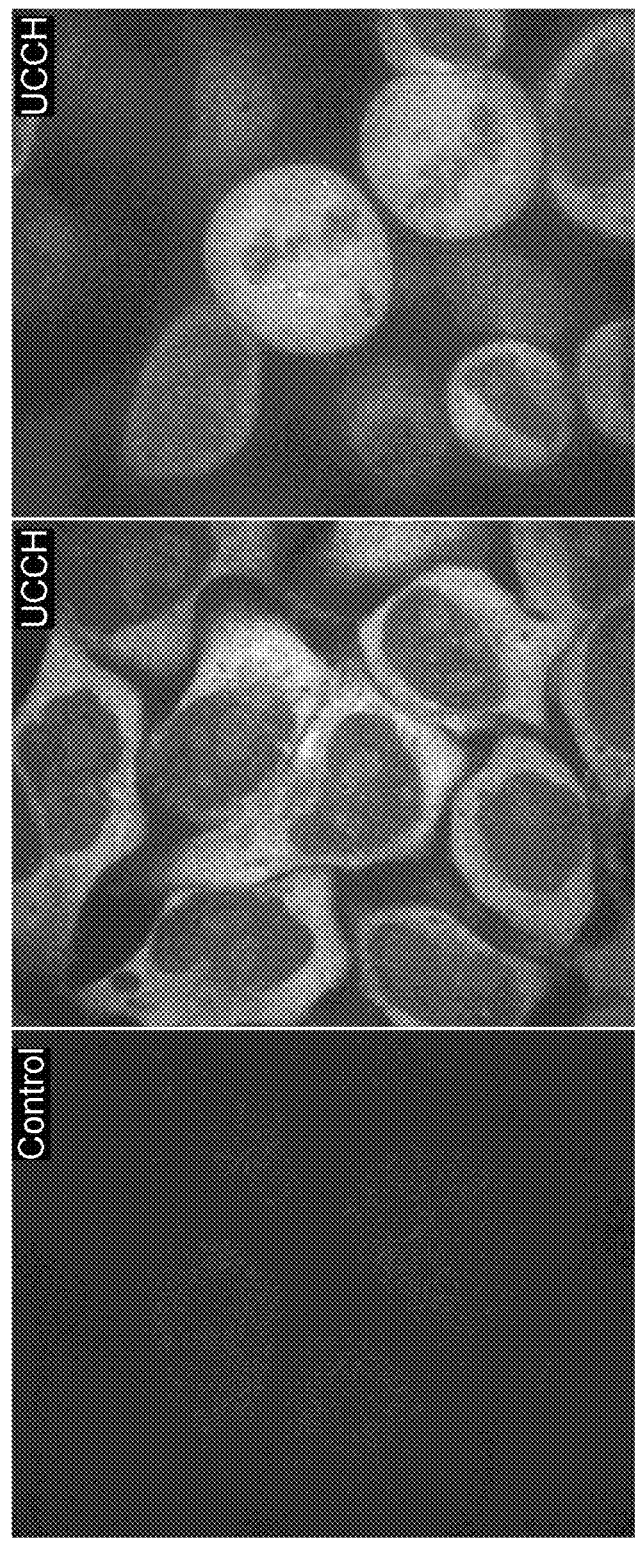
FIG. 14 is a set of three images demonstrating the use of EU (ethynyl-uridine) as a label for cellular RNA. HeLa cells were labeled with 10 μM EU overnight, fixed and stained with Xrhodamine-azide. The image on the left shows cells that were stained with Xrhodamine-azide without having been labeled with EU (negative control). The center and right images are of EU-labeled cells stained with Xrhodamine-azide.
Figure 15:
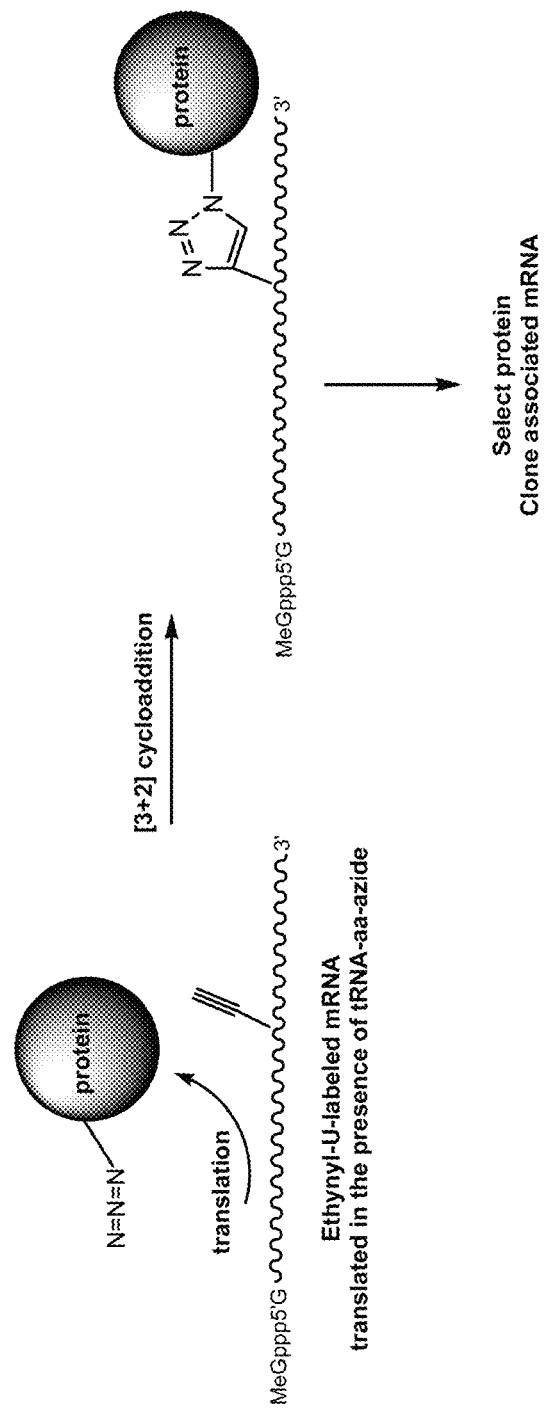
FIG. 15 is a scheme showing ribosome display using a [3+2] cycloaddition according to the present invention.

EU (ethynyl-uridine) was synthesized as a label for cellular RNA. HeLa cells were labeled with 10 µM EU overnight, fixed and stained with Xrhodamine-azide. As shown on FIG. 14, cells that were stained with Xrhodamine-azide without having been labeled with EU (negative control showed very little staining, as expected. EU-labeled cells stained with Xrhodamine-azide exhibited strong cytoplasmic staining indicative of the EU having been incorporated into cellular RNA.

Example 7: Using Azdo-dU (AdU) to Stain HeLa Cells

The 5-azido derivatives of both 2'-deoxyuridine (AdU) and uridine (AU) were synthesized. AdU is a deoxynucleoside analogue that can be used together with EdU to stain DNA with two different colors (if EdU and AdU are administered to cells as two separate pulses and then the detection is done using fluorophore 1-azide and fluorophore 2-terminal alkyne, respectively).

Similarly, AU can be used to label cellular RNA. Cellular RNA can be labeled with two different colors using ethynyl-uridine and azido-uridine, respectively.

Figure 16:
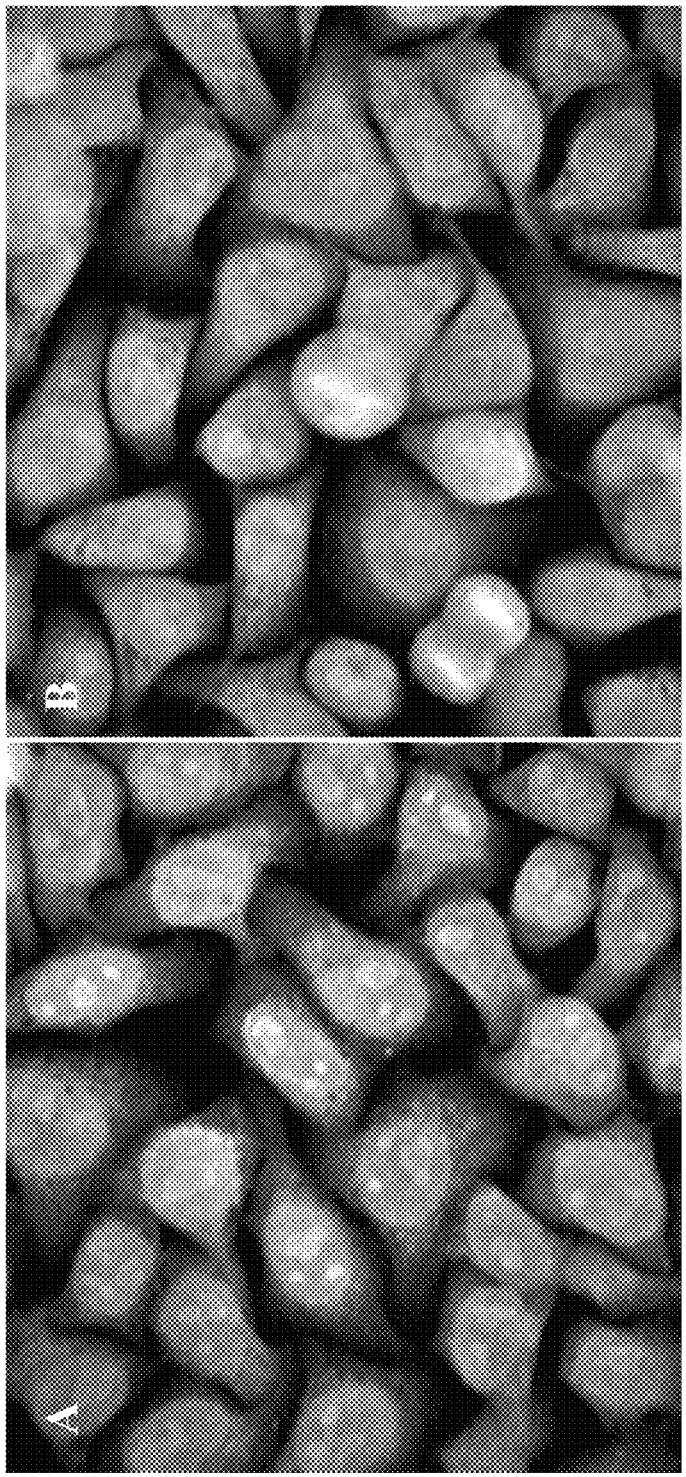
FIG. 16 is a set of two images of a field of HeLa cells labeled with AdU and stained with Alexa568-alkyne (see Example 7 for details). AdU is clearly detected in the nuclei of the labeled interphase cells (A) as well as in the condensed chromosomes of mitotic cells (B).

Here HeLa cells were labeled overnight in 10 µM AdU and then stained with 10 µM Alexa568-alkyne using the conditions described herein for staining cells labeled with EdU. FIG. 16 presents two pictures of a field of the stained HeLa cells. As shown on FIG. 16, AdU is clearly detected in the nuclei of the labeled interphase cells as well as in the condensed chromosomes of mitotic cells.

Example 8: Erasing DNA Staining Under Mild Conditions

In some cases, it is desirable to erase the fluorescent staining of EdU-labeled DNA. A strategy is described here to accomplish that goal.

HeLa cells were labeled with 1 µM EdU overnight and fixed the next day. Staining was performed using 10 µM of an Alexa568-azide (abbreviated Alexa568-SS-azide) that was synthesized by the Applicant in which the azide group was attached to the fluorophore via a cystamine linker ($H_2N$—$CH_2$—$CH_2$—S—S—$CH_2$—$CH_2$—$NH_2$). The disulfide bond in the linker can easily reduced using a reducing agent such as DTT (dithiothreitol), resulting in the dissociation of the fluorophore from the DNA strands.

Figure 17:
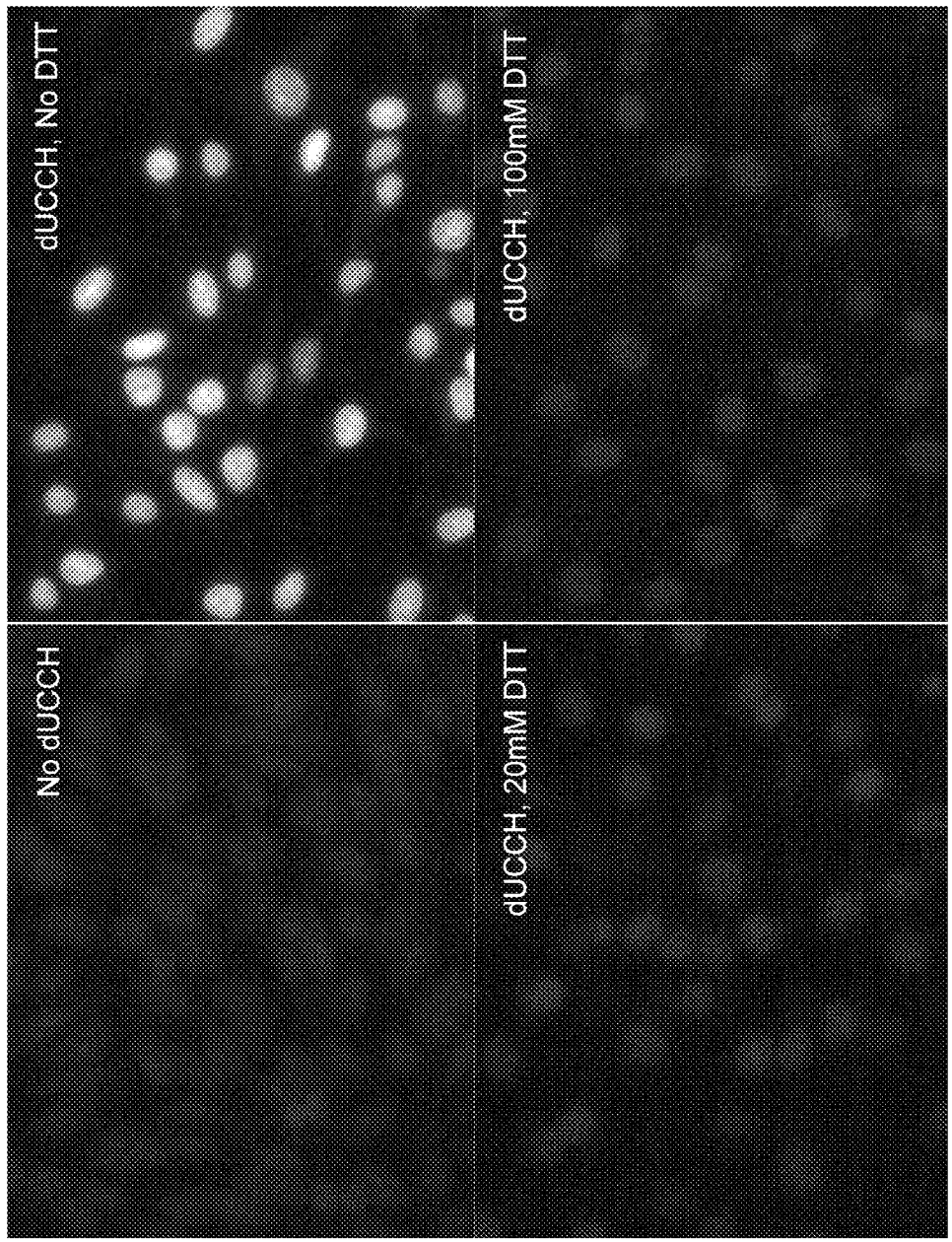
FIG. 17 is a set of four images demonstrating a strategy described herein to effectively remove fluorescent signal from cell nuclei. HeLa cells were either left unstained (first row, left hand side); labeled with EdU and stained with Alexa568-azide (first row, right hand side); labeled with EdU and stained with Alexa568-azide and treated with 20 mM of DTT (second row, left hand side) or 100 mM of DTT (second row, right hand side) (see Example 8 for details).

The second row of FIG. 17 shows pictures of HeLa cells which were incubated with 20 mM (left hand side) and 100 mM (right hand side) of DTT, after the Alexa568-SS-azide stain, as described above. DTT incubation was carried out for 30 minutes at 37° C. The first row of FIG. 17 shows pictures of HeLa cells incubated as described above (i.e., without subsequent DTT incubation) (right panel) and HeLa cells that were not incubated in the presence of EdU and Alexa568-azide (left panel). As shown by the pictures of FIG. 17, DTT incubation effectively removes the fluorescent signal from cell nuclei.

Example 9: General Protocols for Labeling of Cells with Azido-dU Via Staudinger Ligation Azido-dU (AdU) is used in tissue culture media (DMEM complemented with penicillin, streptomycin, and fetal calf serum (FCS)) ranging from 10 nM to 1 µM depending on the length of the labeling pulse. For example, if cells to be labeled are synchronized in the S phase, 100 nM to 1 µM of AdU is used for 1 to 2 hours. After labeling, the cells are washed 3 or 4 times with PBS and then tissue culture media is added.

Staining of Living Cells:

Staining Solution: 100 mM Tris pH 8.5 (from 2 M stock in water), 0.5 to 1 µM a Staudinger ligation-staining reagent (i.e., a molecule comprising a fluorescent moiety attached to a substituted triarylphosphine) (from approximately 100 mM stock in DMF), and water (as required) are mixed together.

For staining cells alive without permeabilization, tissue culture media is removed and replaced by the staining solution described above. Cells are incubated for at least 30 minutes in the presence of the staining solution although staining is generally complete after 10 minutes of incubation. After staining, unreacted staining reagent is removed by washing with buffer (such as PBS or TBS) containing 0.5% Triton-X100 (or similar detergent). Washes with methanol or ethanol may be performed to obtain low background If desired, cell fixation can be performed at the same time by adding 3% formaldehyde (or glutaraldehyde) to the washing buffer. In this case, cells are incubated in the washing buffer for at least 10 minutes at room temperature.

Staining of Fixed Cells:

Cells can be fixed by any suitable method, e.g., cells can be fixed by aldehyde fixation (formaldehyde or glutaraldehyde), with or without permeabilization.

After fixation, the cells are washed in buffer with or without non-ionic detergent (0.2-0.5% Triton X100). Before staining, cells are rinsed with buffer without detergent (PBS or TBS). The cells are then incubated in the presence of the staining solution for at least 30 minutes. Overnight staining is preferably performed in a cold room.

Following staining, the cells are washed several times with a buffer containing 0.5% of detergent. Washes with methanol or ethanol can be performed to significantly reduce the background if necessary.

Stained Cells Imaging:

Stained cells can then be immunostained using standard protocols. Cells are then mounted in standard mounting media and imaged.

Example 10: In Vivo Labeling

BLAB/C mice are injected with 200 micrograms of AdU intraperitoneally. Three days later, organs are harvested, fixed, embedded in paraffin and sectioned. The sections are then de-waxed and stained with a Staudinger ligation-staining reagent (i.e., a molecule comprising a fluorescent moiety attached to a substituted triarylphosphine) for 5 minutes, stained with Hoechst, washed and then mounted.

Example 11: Labeling of RNA in Cells

AU (ethynyl-uridine) was synthesized as a label for cellular RNA. In a RNA staining experiment, HeLa cells are labeled with 10 µM AU overnight, fixed and stained with a Staudinger ligation-staining reagent (i.e., a molecule comprising a fluorescent moiety attached to a substituted triarylphosphine).

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A nucleic acid polymer comprising at least one nucleotide analogue attached to a label, wherein the nucleic acid polymer is prepared by a method of labeling a nucleic acid polymer, comprising steps of:
   providing a nucleic acid polymer comprising at least one nucleotide analogue that comprises an azide group; and
   contacting the nucleic acid polymer with a reagent comprising a label attached to a substituted triarylphosphine, such that a Staudinger ligation occurs between the azide and substituted triarylphosphine;
wherein the nucleic acid polymer is one of the two DNA molecules of a chromosome.

2. A cell comprising a nucleic acid polymer of claim 1.

3. The nucleic acid polymer of claim 1, wherein the nucleic acid polymer is in a living cell.

4. The nucleic acid polymer of claim 1, wherein the nucleic acid polymer is prepared by a method of labeling a nucleic acid polymer, comprising steps of:
   providing a nucleic acid polymer comprising at least one nucleotide analogue that comprises an azide group; and
   contacting the nucleic acid polymer with a reagent comprising a label attached to a substituted triarylphosphine, such that a Staudinger ligation occurs between the azide and substituted triarylphosphine,
   wherein the azide group is attached to the nucleotide analogue at a 5-position of a pyrimidine base.

5. A cell comprising the nucleic acid polymer of claim 4.

6. The nucleic acid polymer of claim 4, wherein the nucleic acid polymer is in a living cell.

7. The nucleic acid polymer of claim 1, wherein the nucleic acid polymer is prepared by a method of labeling a nucleic acid polymer, comprising steps of:
   providing a nucleic acid polymer comprising at least one nucleotide analogue that comprises an azide group; and
   contacting the nucleic acid polymer with a reagent comprising a label attached to a substituted triarylphosphine, such that a Staudinger ligation occurs between the azide and substituted triarylphosphine,
   wherein the azide group is carried on a 5-azido-2'-deoxyuracil unit.

8. A cell comprising the nucleic acid polymer of claim 7.

9. The nucleic acid polymer of claim 7, wherein the nucleic acid polymer is in a living cell.

* * * * *

UNITED STATES PATENT AND TRADEMARK OFFICE
CERTIFICATE OF CORRECTION

PATENT NO. : 10,550,422 B2
APPLICATION NO. : 15/332304
DATED : February 4, 2020
INVENTOR(S) : Kyle R. Gee et al.

Page 1 of 1

It is certified that error appears in the above-identified patent and that said Letters Patent is hereby corrected as shown below:

In the Specification

Column 1, Lines 19-20, please delete:
"Part of the work described herein was funded by the National Institutes of Health (Grant No. GM039565)."

And insert:
--This invention was made with government support under GM039565 awarded by National Institutes of Health (NIH). The government has certain rights in this invention.--

Signed and Sealed this
Sixth Day of December, 2022

Katherine Kelly Vidal
*Director of the United States Patent and Trademark Office*